US005997621A

United States Patent [19]

Scholz et al.

[11] Patent Number: 5,997,621
[45] Date of Patent: *Dec. 7, 1999

[54] COATING COMPOSITION HAVING ANTI-REFLECTIVE AND ANTI-FOGGING PROPERTIES

[75] Inventors: Matthew T. Scholz, Woodbury; William L. Kausch, Cottage Grove; David R. Boston, Woodbury; Joseph M. Zoborowski, Vadnais, all of Minn.

[73] Assignee: Minnesota Mining and Manufacturing Co., St. Paul, Minn.

[ * ] Notice: This patent is subject to a terminal disclaimer.

[21] Appl. No.: 09/168,052

[22] Filed: Oct. 7, 1998

Related U.S. Application Data

[63] Continuation of application No. 08/741,334, Oct. 29, 1996, Pat. No. 5,873,931, which is a continuation of application No. 08/354,242, Dec. 12, 1994, abandoned, which is a continuation-in-part of application No. 08/301,270, Sep. 6, 1994, abandoned, which is a continuation of application No. 08/158,149, Nov. 24, 1993, abandoned, which is a continuation of application No. 07/957,235, Oct. 6, 1992, abandoned, and a continuation-in-part of application No. 08/275,013, Jul. 12, 1994, abandoned, which is a continuation of application No. 08/158,152, Nov. 24, 1993, abandoned, which is a continuation of application No. 07/957,217, Oct. 6, 1992, abandoned.

[51] Int. Cl.$^6$ .............................. B05D 5/06; C09D 1/00; C09D 5/00; C09K 3/18

[52] U.S. Cl. ........................... 106/13; 106/2; 106/287.1; 106/287.11; 106/287.34; 106/287.13; 523/169; 428/429; 428/426; 428/412; 428/447; 428/451; 428/452

[58] Field of Search ........................... 523/169; 428/429, 428/426, 412, 447, 451, 452; 106/2, 287.1, 287.34, 287.11, 287.13, 13; 282/351, 353, 354, 355, 357, 356; 516/34, 81

[56] References Cited

U.S. PATENT DOCUMENTS

| | | | |
|---|---|---|---|
| 2,366,516 | 1/1945 | Geffcken et al. | 117/118 |
| 2,559,629 | 7/1951 | Berry | 260/408 |
| 2,732,398 | 1/1956 | Brice et al. | 260/503 |
| 2,803,552 | 8/1957 | Stedman | 106/13 |
| 2,809,990 | 10/1957 | Brown | 260/534 |
| 3,022,178 | 2/1962 | Park et al. | 106/13 |
| 3,075,228 | 1/1963 | Elias | 15/506 |
| 3,212,909 | 10/1965 | Leigh | 106/13 |
| 3,301,701 | 1/1967 | Baker et al. | |
| 3,816,184 | 6/1974 | Redmore et al. | 148/6.15 |

(List continued on next page.)

FOREIGN PATENT DOCUMENTS

| | | |
|---|---|---|
| 0 372 756 | of 0000 | European Pat. Off. . |
| 0 051 405 A1 | 5/1982 | European Pat. Off. . |
| 0 203 730 | 12/1986 | European Pat. Off. . |
| 427 548 A2 | 5/1991 | European Pat. Off. . |
| 451 893 A1 | 10/1991 | European Pat. Off. . |
| 0 460 382 A2 | 12/1991 | European Pat. Off. . |
| 24 46 279 | 1/1976 | Germany . |
| 29 47 823 | 6/1980 | Germany . |
| 29 49 168 C2 | 7/1980 | Germany . |
| 58-126502 | 7/1983 | Japan . |
| 61-053038 | 3/1986 | Japan . |
| 62-129366 | 6/1987 | Japan . |
| 63-014141 | 1/1988 | Japan . |
| 63-179966 | 7/1988 | Japan . |
| 2-022342 | 1/1990 | Japan . |
| 2-022343 | 1/1990 | Japan . |
| 2-022344 | 1/1990 | Japan . |
| 3-101926 | 4/1991 | Japan . |
| 5-59203 | 3/1993 | Japan . |
| 5-59300 | 3/1993 | Japan . |
| WO 89/04362 | 5/1989 | WIPO . |
| WO 89/10106 | 11/1989 | WIPO . |
| WO 96/18691 | 6/1996 | WIPO . |
| WO 96/18918 | 6/1996 | WIPO . |
| WO 97/23571 | 7/1997 | WIPO . |

OTHER PUBLICATIONS

ASTM Test Method D1003–92, entitled "Standard Test Method for Haze and Luminous Transmittance of Transparent Plastics" (Reapproved 1988). no month.

Bragg et al., "The Form Birefringence of Macromolecules", *Acta Cryst.*, 6 (1953). no month.

Cathro et al., "Silica Low–Reflection Coatings for Collector Covers, by a Dip–Coating Process", *Solar Energy*, 32, (5) (1984). no month.

Masso, "Evaluation of Scratch Resistant and Antireflective Coatings for Plastic Lenses", Society of Vacuum Coaters, Proceedings of the 32$^{nd}$ Annal Technical Conference, Apr. 24–28, 1989, Copyright 1989, Society of Vacuum Coaters. no month.

Milwidsky, "Non–Conventional Surface Active Agents", *Household & Personal Products Industry*, (1981). no month.

Product literature—"Fluorad™, Fluorochemaical Specialties, Fluorad Lithium Trifluoromethanesulfonimide Battery Electroyte HQ–115", 3M Industrial Chemical Products Division, May 1992.

Product literature—"Fluorad™, Fluorochemical Surfactants, Fluorad™ Fluorochemical Surfactant FC–127", 3M Industrial Chemical Products Division, Mar. 1987.

Product literature—"AGAFAR™ Adjustable Flip–Up Face Shields", Infection Control Products, Inc. (1993). no month.

Product literature—"Fluorad™ Coating Additives FC–430 and FC–431", 3M Industrial Chemical Products Division (Nov. 1989).

Trotoir, "Antifog/antistat eases processing problems", *Modern Plastics*, (Oct. 1988).

"SURFLOW", Product Brochure from AGC (Agahi Glass Company), pp. 4–10 (Undated). [Japanese—no English Translation].

*Primary Examiner*—C. Melissa Koslow
*Attorney, Agent, or Firm*—Robert W. Spraque; Jeffrey J. Hohenshell

[57] ABSTRACT

A coating composition which imparts anti-reflective and anti-fog properties to substrates coated therewith. The coating composition utilizes an inorganic metal oxide in combination with particular anionic surfactants. The coating compositions are particularly useful in the manufacture of disposable surgical masks and face shields.

62 Claims, No Drawings

U.S. PATENT DOCUMENTS

| | | | |
|---|---|---|---|
| 3,819,522 | 6/1974 | Zmoda et al. | 252/89 |
| 3,826,127 | 7/1974 | Molina | 73/67.5 R |
| 3,833,368 | 9/1974 | Land et al. | 96/3 |
| 3,864,132 | 2/1975 | Rasch et al. | 96/85 |
| 3,897,356 | 7/1975 | Pociluyko | 252/91 |
| 3,986,997 | 10/1976 | Clark | 260/29.2 M |
| 4,190,321 | 2/1980 | Dorer et al. | 350/167 |
| 4,235,638 | 11/1980 | Beck et al. | 106/287.12 |
| 4,264,707 | 4/1981 | Uozumi et al. | 430/279 |
| 4,271,210 | 6/1981 | Yoldas | 427/169 |
| 4,273,826 | 6/1981 | McCollister et al. | 428/304 |
| 4,275,118 | 6/1981 | Baney et al. | 428/412 |
| 4,284,685 | 8/1981 | Olson et al. | 428/331 |
| 4,309,319 | 1/1982 | Vaughn, Jr. | 260/8 |
| 4,310,330 | 1/1982 | Funaki et al. | 8/506 |
| 4,340,276 | 7/1982 | Maffitt et al. | 350/164 |
| 4,344,860 | 8/1982 | Pleuddemann | 252/389 R |
| 4,346,131 | 8/1982 | Yoldas | 428/33 |
| 4,370,255 | 1/1983 | Pleuddemann | 252/389 A |
| 4,374,158 | 2/1983 | Taniguchi et al. | 427/41 |
| 4,409,285 | 10/1983 | Swerdlow | 428/332 |
| 4,446,171 | 5/1984 | Thomas | 427/160 |
| 4,467,073 | 8/1984 | Creasy | 525/127 |
| 4,478,909 | 10/1984 | Taniguchi et al. | 428/331 |
| 4,505,997 | 3/1985 | Armand et al. | 429/192 |
| 4,610,955 | 9/1986 | Chen et al. | 430/527 |
| 4,731,264 | 3/1988 | Lin et al. | 427/387 |
| 4,816,333 | 3/1989 | Lange et al. | 428/331 |
| 4,895,767 | 1/1990 | Mori et al. | 428/447 |
| 4,941,988 | 7/1990 | Wise | 252/99 |
| 4,944,294 | 7/1990 | Borek, Jr. | 128/206.19 |
| 5,020,533 | 6/1991 | Hubbard et al. | 128/206.23 |
| 5,021,091 | 6/1991 | Takarada et al. | 106/287.16 |
| 5,021,308 | 6/1991 | Armand et al. | 429/194 |
| 5,049,414 | 9/1991 | Kato | 427/164 |
| 5,100,503 | 3/1992 | Allman et al. | 156/643 |
| 5,134,021 | 7/1992 | Hosono et al. | 428/213 |
| 5,150,703 | 9/1992 | Hubbard et al. | 128/206.12 |
| 5,204,219 | 4/1993 | Van Ooij et al. | 430/272 |
| 5,242,887 | 9/1993 | Usui | 503/227 |
| 5,449,702 | 9/1995 | Tayama et al. | 522/4 |
| 5,476,717 | 12/1995 | Floch | 428/421 |
| 5,523,649 | 6/1996 | Tong et al. | 313/479 |
| 5,585,186 | 12/1996 | Scholz et al. | 106/287.16 |
| 5,723,175 | 3/1998 | Scholz et al. | 427/161 |
| 5,753,373 | 5/1998 | Scholz et al. | 428/429 |

5,997,621

COATING COMPOSITION HAVING ANTI-REFLECTIVE AND ANTI-FOGGING PROPERTIES

This is a continuation of U.S. patent application Ser. No. 08/741,334 filed Oct. 29, 1996, now U.S. Pat. No. 5,873,931, which is a continuation of application Ser. No. 08/354,242, filed Dec. 12, 1994, abandoned; which is a continuation-in-part of U.S. patent application Ser. No. 08/301,270, filed Sep. 6, 1994, abandoned; which is a continuation of U.S. application Ser. No. 08/158,149, filed Nov. 24, 1993, abandoned; which is a continuation of U.S. application Ser. No. 07/957,235 filed Oct. 6, 1992 abandoned, and a continuation-in-part of U.S. application Ser. No. 08/275,013, filed Jul. 12, 1994 abandoned; which is a continuation of U.S. application Ser. No. 08/158,152, filed Nov. 24, 1993, abandoned; which is a continuation of U.S. application Ser. No. 07/957,217 filed Oct. 6, 1992, abandoned.

TECHNICAL FIELD

This invention relates generally to coating compositions and methods for producing optically clear articles with very low reflection and exceptional anti-fogging properties even under high humidity conditions. Such properties are desirable in articles such as face shields used for personal protection, ophthalmic lenses, architectural glazings, windows, automotive windshields and the like.

BACKGROUND ART

There are numerous instances where optically clear articles would be enhanced if the tendency of the articles to cause glare or to be obscured by the formation of a fog on a surface of the article could be reduced. For example, protective eyewear (goggles, face shields, helmets, etc.), ophthalmic lenses, architectural glazings, decorative glass frames, motor vehicle windows and windshields may all reflect light in a manner that causes an annoying and disruptive glare. Use of such articles may also be detrimentally affected by the formation of a moisture vapor fog on a surface of the article.

Glare is the undesirable reflection of light from a surface upon which the light is incident. In general, glare may be reduced by increasing the amount of light transmitted by the article, thereby reducing the amount of light which is available for reflection. Alternatively, the article surface can be modified (e.g., roughened, embossed, etc.) to cause the light to be reflected from the article more randomly and, therefore, with less glare.

Coatings which significantly increase the percent transmission of light and provide articles having very low reflection ("anti-reflective coatings") are known in the art. For example, U.S. Pat. No. 4,816,333 to Lange et al. (also assigned to 3M) discloses anti-reflective coatings of silica particles. The coating solution contains colloidal silica particles and optionally a surfactant ("Triton™ X-100" and "Tergitol TMN-6") to improve the wettability of the coating solution. U.S. Pat. No. 4,374,158 (Taniguchi et al.) discloses an anti-reflective coating using a gas phase treatment technique. The coating may optionally contain additives as surface controlling agents, such as silicone type surfactants. Various other types of anti-reflective coatings are disclosed in U.S. Pat. Nos. 2,366,516; 3,301,701; 3,833,368; 4,190,321, 4,271,210; 4,273,826; 4,346,131 and 4,409,285; by Cathro et al. in "Silica Low-Reflection Coatings for Collector Covers by a Dye-Coating Process," Solar Energy, Vol. 32, No. 5, pp. 573–579 (1984); and by J. D. Masso in "Evaluation of Scratch Resistant and Anti-reflective Coatings for Plastic Lenses," Proceedings of the 32nd Annual Technical Conference of the Society of Vacuum Coaters, Vol. 32, p. 237–240 (1989). None of these anti-reflective coatings produce a durable anti-fog coating.

In general, fog formation occurs under conditions of high humidity and high temperature or at interfacial boundaries where there is a large temperature and humidity difference. Coatings which reportedly reduce the tendency for surfaces to "fog up" (i.e., anti-fogging coatings) are known. For example, U.S. Pat. No. 3,212,909 to Leigh discloses the use of ammonium soap, such as alkyl ammonium carboxylates in admixture with a surface active agent which is a sulfated or sulfonated fatty material, to produce an anti-fogging composition. U.S. Pat. No. 3,075,228 to Elias discloses the use of salts of sulfated alkyl aryloxypolyalkoxy alcohol, as well as alkylbenzene sulfonates, to produce an anti-fogging article useful in cleaning, and imparting anti-fog properties to various surfaces. U.S. Pat. No. 3,819,522 to Zmoda, discloses the use of surfactant combinations comprising derivatives of decyne diol as well as surfactant mixtures which include ethoxylated alkyl sulfates in an anti-fogging window cleaner surfactant mixture.

Japanese Patent Kokai No. Hei 6[1994]-41335 discloses a clouding and drip preventive composition comprising colloidal alumina, colloidal silica and an anionic surfactant.

U.S. Pat. No. 4,478,909 (Taniguchi et al.) discloses a cured anti-fogging coating film which comprises polyvinyl alcohol, a finely divided silica, and an organic silicon compound, the carbon/silicon weight ratio apparently being important to the film's reported anti-fogging properties. Various surfactants, including fluorine-containing surfactants, may be used to improve the surface smoothness of the coating.

Other anti-fog coatings incorporating surfactants are described in U.S. Pat. Nos. 2,803,552; 3,022,178 and 3,897,356. "Anti-fog Antistat Eases Processing Problems," Modern Plastics, October 1988, discusses antistat agents, including alkyl sulfonates, and anti-fog agents for use in plastic films. Furthermore, American Cyanamid Industrial Chemical Division markets "Aerosol™ OT Surface Active Agent" (dioctylsodium-sulfosuccinate), which is advertised as useful to prepare an anti-fog composition for direct application to glass.

None of the above-described coatings which reduce the tendency for an article to fog have anti-reflective properties. Furthermore, in general, the anti-fog compositions of the prior art rely on high solution concentrations (e.g., in excess of 0.2 percent, and typically in concentrations in excess of 5 percent by weight) of surfactant and other organic additives to provide an anti-fog effect. When used at such high concentrations, the surfactants and other organic additives would interfere with and significantly reduce the anti-reflective properties provided by porous coatings, such as metal oxides.

Face masks and shields which are described as having anti-fog and anti-glare properties are known. For example, the "SHIELDMATE" by IREMA U.S.A. Ltd. of Chicopee, M. A. is described in U.S. Pat. No. 4,944,294 (Borek). The hospital face mask is described as including a transparent plastic eye shield coated with any suitable anti-fogging, anti-glare silicone agent, such as a dimethylsiloxane polymer.

World Patent Application No. 89/10106 (Russell) discloses a surgical mask/face shield combination. The face shield is coated with an anti-fog coating, such as that described in U.S. Pat. No. 4,467,073. These coatings are made by combining, for example, polyvinylpyrrolidone, a surfactant, and a curable isocyanate functional prepolymer. Additionally, Infection Control Products, Inc., markets the "AGAFAR™ Adjustable Flip-Up Face Shield" which is advertised as being anti-glare, anti-fog and anti-reflective. However, none of these products utilize a porous coating and none display an increase in transmission of visible light through the coated article of more than 2 to 3 percent greater than the uncoated article. It is understood that an increase in percent transmission corresponds to a decrease in percent reflection, provided the sample is transparent (i.e., non-light-absorbing and not hazy). Accordingly, a need exists for a coating composition which will impart anti-fog properties to a substrate coated therewith, while increasing the percent transmission, and correspondingly decreasing the percent reflection, of incident light through the substrate, such that the substrate is truly "anti-reflective."

SUMMARY OF THE INVENTION

The present invention provides coating compositions which impart both anti-reflection and anti-fog properties to substrates coated therewith. By "anti-reflective" it is meant that the percent transmission of a light transmissive substrate coated with the coating composition is increased by at least 3 percent over the uncoated substrate measured using 550 nm light. The coating composition utilizes an inorganic metal oxide in combination with particular anionic surfactants which are present in a concentration which imparts a durable anti-fog property to the coated substrate, yet does not destroy the anti-reflective properties provided by the metal oxide.

The present invention provides a coating composition comprising:

(a) a porous inorganic metal oxide;

(b) a surfactant comprised of at least one hydrophobic group and at least one covalently bonded hydrophilic anionic group, wherein (i) the hydrophilic anionic group comprises an anion selected from the group consisting of $-OSO_2O^-$, $-SO_2O^-$, $-CO_2^-$, $(-O)_2P(O)O^-$, $-OP(O)(O^-)_2$, $-P(O)(O^-)_2$, $-P(O^-)_2$, $OP(O^-)_2$, $(-SO_2)_2N^-$, $-SO_2N(R)^-$, $(-SO_2)_2C^-H$, and $-N^+(R)_2(CH_2)_xL'$, wherein R is hydrogen, an alkyl group which is unsubstituted or substituted with atoms independently selected from the group consisting of oxygen, nitrogen and sulfur, or an alkylene carboxyl group, which alkyl or alkylene carboxyl group comprises about 1 to 10 carbon atoms; x is 1 to 4; and L' is selected from the group consisting of $-OSO_2O^-$, $-SO_2O^-$, $(-O)_2P(O)O^-$, $-OP(O)(O^-)_2$, $-P(O)(O^-)_2$ and $-CO^-_2$; and wherein each anionic group is associated with or covalently bound to at least one cation, which cation is selected from the group consisting of $H^+$, $Na^+$, $K^+$, $Li^+$, $Ca^{+2}$, $Mg^{+2}$, $Sr^{+2}$, $Al^{+3}$, and R"A, wherein R" is R or R' wherein R is hydrogen or an alkyl or cycloalkyl group of about 1 to 10 carbon atoms, and R' is covalently bonded to the surfactant molecule and is an alkyl bridging group of 1 to 10 carbon atoms, and A is $N^+R_3$, a guanidinium ion optionally substituted with oxygen, nitrogen or sulfur atoms, or $N^+B$ wherein B comprises 3 to 7 atoms selected from the group consisting of carbon, nitrogen, sulfur and oxygen atoms which complete the nitrogen containing heterocyclic ring; and wherein any R or R' group may be unsubstituted or substituted with atoms independently selected from the group consisting of oxygen, nitrogen or sulphur; the cation being selected such that the net charge of the surfactant molecule is neutral; and (ii) wherein the hydrophobic group comprises a hydrocarbon chain comprising at least 4 carbon atoms or a perfluorinated radical group comprising at least 3 carbon atoms, and wherein the coating composition when coated on at least one side of a light transmissive substrate:

1) exhibits a drop diameter of at least 4 mm when tested in accordance with the Wetting Test described herein; and 2) provides said substrate with a percent transmission at 550 nm which is at least 3 percent greater than that of the uncoated substrate.

The compositions may optionally contain a coupling agent (e.g. a silane) and/or a polymeric binder that improves adhesion of the dried coating to the substrate.

Preferred coating compositions applied to at least one side of a light transmissive substrate increase the percent transmission of the substrate by at least 5 percent, and preferably by 10 percent, while resisting fogging even upon exposure to "steam," i.e., warm air saturated with water. The anti-fog property is shelf stable and deteriorates very slowly when exposed to accelerated aging conditions, as described hereinafter. Ideally, in preferred embodiments, the coated articles have exceptional anti-fog properties while also having greater than 96 percent transmission of 550 nm light.

The compositions may be applied to a wide variety of substrates by a variety of coating methods. Accordingly, the invention provides protective eyewear, such as surgical masks and face shields, as well as ophthalmic lenses, windows and windshields which have anti-reflective and anti-fog properties.

The invention also relates to a method of imparting anti-reflection and anti-fogging properties to a substrate. The method comprises the steps of providing a substrate, preparing a coating composition having the formulation described above, applying the coating composition to the substrate, and drying the coating composition.

DETAILED DESCRIPTION OF THE PREFERRED EMBODIMENTS

Anti-Reflection

The anti-reflective properties of the coatings of this invention are provided by a porous inorganic metal oxide network. More particularly, the coating compositions of the invention when coated on a substrate and dried provide a continuous and highly porous network of metal oxide particles. As used herein, the term "continuous" refers to a coating having no visible discontinuities or gaps. The term "network" (as used herein) refers to a porous, three-dimensional structure, preferably formed by an aggregation of colloidal particles linked together. The network is held together through particle/particle, particle/coupling agent or particle/coupling agent/particle bonds, providing a coating having integrity which does not flake off by simple flexing and/or use of the coated article.

The term "porous" refers to the presence of voids between the inorganic metal oxide particles created when the particles pack together. For single layer coatings, it is known that in order to maximize light transmission in air through an optically transparent substrate, and minimize reflection by the substrate, the refractive index of the coating should equal as closely as possible the square root of the refractive index of the substrate and the thickness of the coating should be one-fourth (¼) of the optical wavelength of the incident light. The voids in the coating provide a multiplicity of subwavelength interstices between the metal oxide particles where the index of refraction (IR) abruptly changes from that of air (IR=1) to that of the metal oxide particles (e.g., for silica IR=1.44). By adjusting the porosity, a coating having a calculated index of refraction (as shown in U.S. Pat. No. 4,816,333 (Lange, et al.) incorporated herein by reference) very close to the square root of the refractive index of the substrate can be created. By utilizing coatings having optimal indices of refraction, at coating thicknesses equal to approximately one-fourth the optical wavelength of the incident light, the percent transmission of light through the coated substrate is maximized and reflection is minimized.

The voids in the coating are present substantially throughout; however, the coating may vary in density, e.g., the coating may become gradually more porous moving away from the substrate producing a gradient density. Such a gradient density enhances the anti-reflective property of the coating. Preferably, the network has a porosity of about 25 to 45 volume percent, more preferably about 30 to 40 volume percent, when dried. Porosity may be calculated from the refractive index of the coating according to published procedures such as in W. L. Bragg, A. B. Pippard, *Acta Crystallographica*, volume 6, page 865 (1953) incorporated herein by reference. When the metal oxide is silicon dioxide, this porosity provides a coating having an index of refraction of 1.2 to 1.4, preferably 1.25 to 1.36, which is approximately equal to the square root of the refractive indices of polyester, polycarbonate, or polymethyl methacrylate substrates. For example, a porous silica coating having a refractive index of 1.25 to 1.36 is capable of providing a highly anti-reflective surface when coated on a polyethylene terephthalate substrate (IR=1.64) at a thickness of 1000–1200 Å.

The metal oxide component of the present invention is preferably silica (essentially silicon dioxide with or without other additives or impurities) but may alternatively be aluminum oxide, tin oxide, titanium oxide, antimony oxide, zirconium oxide, as well as mixtures and combinations thereof. The metal oxide particles should be less than about 200 nm in diameter in order to provide effective anti-reflective properties. Preferably the average particle diameter is less than 70 nm, more preferably less than 20 nm, and most preferably between about 4 and 8 nm. Although the particles are preferably spherical, other shapes are possible including irregular and fibrous shapes. The metal oxide concentration is preferably from about 0.1 to 15 percent by weight of the coating solution, more preferably from about 0.5 to 5 percent by weight. Above about 15 percent by weight the coating solution becomes difficult to apply in the desired thickness range and below about 0.1 percent by weight, excessive time periods are required for the coating to dry after application to the substrate. The term "solution" as used herein includes dispersions or suspensions of finely divided inorganic metal oxide particles in a liquid medium.

The metal oxide is most conveniently coated on the substrate as a colloidal dispersion (referred to herein as a "sol") which comprises finely divided solid inorganic metal oxide particles in an aqueous or an organic liquid. The sol may be acid or base stabilized. Sodium hydroxide base stabilized sols having a pH of 9 to 11 are most preferred and include "NALCO 1115" and "NALCO 1130," commercially available from NALCO Chemical Co., "Remasol SP30," commercially available from Remet Corp., and "LUDOX SM," commercially available from E. I. Du Pont de Nemours Co., Inc.

Anti-Fog

The coating compositions of the present invention provide anti-fog properties, in addition to anti-reflection, to substrates coated therewith. Coatings are considered anti-fogging if a coated substrate resists the formation of small, condensed water droplets in sufficient density to significantly reduce the transparency of the coated substrate such that it cannot be adequately seen through, after exposure to repeated human breathing directly on the article and/or after holding the article above a "steam" jet. A coating composition may still be regarded as anti-fogging even though a uniform water film or a small number of large water droplets forms on the coated substrate so long as the transparency of the coated substrate is not significantly reduced such that it cannot be readily seen through. In many instances, a film of water that does not significantly reduce the transparency of the substrate will remain after the substrate has been exposed to a "steam" jet.

The compositions of the present invention derive their anti-fogging property by incorporation of a particular surfactant or combination of surfactants. The term "surfactant" as used herein describes molecules comprising hydrophilic (polar) and hydrophobic (non-polar) regions on the same molecule which are sizeable enough to be capable of reducing the surface tension of the coating solution and providing a coating which imparts anti-fog properties to substrates or articles coated therewith. Certain surfactants of the present invention comprise multiple hydrophilic and or hydrophobic regions on the same molecule.

Useful surfactants comprise at least one hydrophilic anionic group. The anionic group may be $-OSO_2O^-$, $-SO_2O^-$, $-CO_2-$, $(-O)_2P(O)O^-$, $-P(O)(O^-)_2$, $-P(O)(O^-)_2$, $-P(O^-)_2$, $-OP(O^-)_2$, $(-SO_2)_2N^-$, $-SO_2N(R)^-$, $(-SO_2)_2C^-H$ or $-N^+(R)_2(CH_2)_xL'$, wherein R is hydrogen, an alkyl group which is unsubstituted or substituted with atoms independently selected from the group consisting of oxygen, nitrogen and sulfur or an alkylene carboxyl group, which alkyl or alkylene group comprises about 1 to 10 carbon atoms; x is 1 to 4; and L' is selected from the group consisting of $-OSO_2O^-$, $-SO_2O^-$, $(-O)_2P(O)O^-$, $-OP(O)(O^-)_2$, $-P(O)(O^-)_2$ and $-CO^-_2$. Each anionic group is associated with at least one cation such that the ratio of total anionic charge of the surfactant molecule, to the total cationic charge of the surfactant molecule equals 1, making the net charge of the surfactant molecule neutral. The cation(s) are selected from the group consisting of hydrogen, sodium, potassium, lithium, ammonium, calcium, magnesium, aluminum, strontium and R"A groups, wherein R" is R or R', wherein R is hydrogen or an alkyl or cycloalkyl group of about 1 to 10 carbon atoms, and R' is covalently bonded to the surfactant molecule and is an alkyl bridging group of 1 to 10 carbon atoms, and A is $N^+R_3$, a guanidinium ion optionally substituted with oxygen, nitrogen or sulfur atoms, or $N^+B$ wherein B comprises 3 to 7 atoms selected from the group consisting of carbon, nitrogen, sulfur and oxygen atoms which complete the nitrogen containing heterocyclic ring; and wherein any R or R' group may be unsubstituted or substituted with oxygen, nitrogen or sulfur atoms. Of course, cations having a charge greater than one may be associated with more than one anion, e.g., $-(SO_4)_2Ca$ or $-(SO_3)_2Mg$. The anionic group may be the sole hydrophilic group or may be covalently bound to other hydrophilic groups such as ester, thio ester, ether, amide, urea, urethane, hydroxyl and amine groups and polymers comprising these groups and having molecular weights less than about 5,000, and preferably less than about 2,000 (e.g., an anionic derivative of a polyethoxylated surfactant).

Applicants have found that useful surfactants having a carboxylate group as the hydrophilic group further comprise an additional polar substituent capable of stabilizing the ionic form of the surfactant. Preferably, the additional polar substituent is no further than three or four atoms removed from the carbon of the carboxylate group. The added polar substituent is preferably an ether, amide, alcohol, carboxyl, ester, urea or urethane group.

The anionic property of the surfactants of the present invention is an important one. Applicants have found that surfactants such as the nonionic surfactants based on repeating units of ethylene oxide and propylene oxide (e.g., "Pluronic™ Block Copolymer Surfactants" and "Tetronic™ Block Copolymer Surfactants," both commercially available from BASF Corp., Performance Chemicals, Parsippany, N.J.), as well as those based on tetramethyldecyne diol (e.g., "Surfynol 104," commercially available from Air Products and Chemicals, Inc., Allentown, Pa.), do not produce a durable anti-fog coating when used with porous metal oxide networks. Additionally, polyethoxylated alcohols, such as "Tergitol® TMN-6," commercially available from Union Carbide Chemical and Plastics Co., Industrial Chemicals Division, Danbury, Conn., polyethoxylated alkyl phenols, such as "TRITON® X-100," also commercially available from Union Carbide, and amine oxides, such as "Rhodamox LO," commercially available from Rhone-Poulenc, Surfactant and Specialty Division, Dalton, Ga., do not produce durable anti-fog coatings when used with porous metal oxide networks. Cationic surfactants such as 3-lauramidopropyltrimethyl-ammonium methosulfate (commercially available as "Cyastat® LS Antistatic Agent", from Cytec Industries, Stamford, Conn.) and myristyl trimethylammonium bromide also do not produce durable anti-fog coatings when used with porous metal oxide networks.

Useful surfactants comprise at least one hydrophobic group which comprises a hydrocarbon chain comprising at least four carbon atoms, or a perfluorinated group comprising at least three carbon atoms. Surfactants containing a perfluorinated group preferably include a perfluorinated radical group of at least six carbons, more preferably at least eight carbon atoms. Surfactants which do not include a perfluorinated group preferably have a hydrocarbon chain of at least eight, and more preferably, at least twelve carbon atoms.

The surfactants of the present invention in order to be immobilized on the substrate at room temperature, preferably also possess at least one of the following characteristics.

1. The surfactant has a melting point greater than room temperature, i.e., greater than about 20° C., preferably greater than about 30° C., and most preferably greater than 40° C.

2. The surfactant is relatively insoluble in water. Preferably the surfactant has a solubility in water of less than about 10 percent by weight, more preferably less than about 1 percent by weight and most preferably less than about 0.1 percent by weight, at 23° C. Relatively insoluble surfactants are preferred since they are less likely to rehydrate, dissolve, and reorient, even under high humidity conditions.

3. The surfactant is capable of being covalently bound to metal oxide. The surfactant may itself react with the metal oxide, or may be chemically bound to the metal oxide through the use of a coupling agent, as described in further detail hereinbelow.

Surfactant Chemistry

The surfactants useful in the practice of this invention have the following general structure:

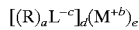

wherein:
R is a perfluorinated alkyl or cycloalkyl group of about 3 to 18 carbon atoms; a polyethoxylated perfluoroalkyl or perfluorocycloalkyl substituted alcohol comprising about 3 to 18 perfluorinated carbon atoms and about 0 to 30 non-fluorinated carbon atoms; a perfluoroalkyl substituted alkyl or alkenyl group of about 3 to 18 perfluorinated atoms and about 0 to 30 non-fluorinated carbon atoms, which alkyl or alkenyl group optionally comprises oxygen, nitrogen or sulfur atoms within or substituted upon the alkyl or alkenyl chain; an alkyl or alkenyl group (straight or branched chain) of about 4 to 36 carbon atoms, which alkyl or alkenyl group optionally comprises oxygen, nitrogen or sulfur atoms within or substituted upon the alkyl or alkenyl chain; an aralkyl group of about 7 to 36 carbon atoms, which aralkyl group is optionally independently substituted in available positions by oxygen, nitrogen or sulfur atoms; or a polyethoxylated or polypropoxylated alkyl or aralkyl group which alkyl or aralkyl group comprises about 7 to 36 carbon atoms;

L is a sulfate ($-OSO_2O^-$), sulfonate ($-SO_2O^-$), phosphate (($-O)_2P(O)O^-$ or $-OP(O)(O^-)_2$), phosphonate ($-P(O)(O^-)_2$), sulfonimide (($-SO_2)_2N^-$), sulfonamide ($-SO_2N(R')^-$), carboxylate ($-CO_2^-$), phosphonite ($-P(O^-)_2$), phosphite ($-OP(O^-)_2$), or disulfonylmethide (($-SO_2)_2C^-H$). Amphoteric alkyl forms of the above groups are also useful, including groups having the formula $-N^+(R''')_2(CH_2)_xL'$, wherein R''' is hydrogen or an alkyl or alkylene group optionally substituted with nitrogen, oxygen or sulfur atoms; or an alkylene carboxyl group, which alkyl or alkylene carboxyl group comprises about 1 to 10 carbon atoms; x=1 to 4; and L' is $-OSO_2O^-$, $-SO_2O^-$, $(-O)_2P(O)O^-$, $-OP(O)(O^-)_2$, $-P(O)(O^-)_2$, $-CO_2^-$, $-P(O^-)_2$, or $-OP(O^-)_2$; provided that when L is a carboxylate, R further comprises an additional polar heteroatom or substituent no further than four, and preferably no further than three, atoms removed from the carboxylate group wherein said polar substituent is an ether, amide, alcohol, carboxyl, ester, thioester, urea, or urethane group, or combinations thereof including oligomers comprising these polar groups;

M is hydrogen ($H^+$), sodium ($Na^+$), potassium ($K^+$), lithium ($Li^+$), ammonium ($NH_4^+$), calcium ($Ca^{+2}$), magnesium ($Mg^{+2}$), strontium ($Sr^{+2}$), aluminum ($Al^{+3}$) or R''$A^+$, wherein R'' is R or R', wherein R is hydrogen or an alkyl or cycloalkyl group of about 1 to 10 carbon atoms and R' is covalently bonded to the surfactant molecule and is an alkyl bridging group of about 1 to 10 carbon atoms, and $A^+$ is selected from the group consisting of $N^+R_3$, (e.g., $N^+(CH_3R)_4$, $HN^+(CH_2CH_2OH)_3$, $H_2N(CH_2CH_2OH)_2$); a guanidinium ion optionally substituted with oxygen, nitrogen or sulfur atoms; or a heterocyclic $N^+B$ wherein B comprises 3 to 7 atoms selected from the group consisting of carbon, nitrogen, sulfur and oxygen atoms which complete the nitrogen containing heterocyclic ring; and wherein R' and R may be substituted in available positions with oxygen, nitrogen or sulfur atoms;

a and c are independently 1 or 2;

b and d are independently 1, 2 or 3; and e is equal to (c times d)/b, or 0 in the case of amphoteric surfactants.

When R is a polyethoxylated or polypropoxylated substituent or a copolymer of ethylene oxide and propylene oxide, wherein these polymeric subunits are present in amounts of 1 to 100 moles, preferably about 1 to 20 moles per mole of surfactant.

The following surfactant classes and surfactants are particularly useful individually or in combination in the practice of the present invention:

1. Perfluoroaliphatic Anionic Salts

Surfactants within this class are of the general formula described above wherein:

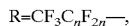

and wherein n is about 2 to 17, preferably about 3 to 12.

Preferred surfactants within this class include the lithium, sodium and potassium salts of anionic perfluoroaliphatic radical containing compounds. Some particularly preferred lithium salts include the following:

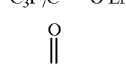

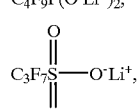

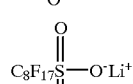

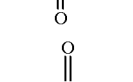

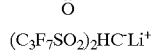

Useful lithium salts are made following techniques disclosed in, for example, U.S. Pat. No. 2,732,398 (Brice et al.) and U.S. Pat. No. 2,809,990 (Brown), both incorporated herein by reference. Examples of commercially available lithium salts of anionic perfluoroaliphatic radical containing compounds include "Fluorad™ FC-122," "Fluorad™ FC-123" and "Fluorad™ FC-124 Fluorochemical Surfactants," from 3M Company, St. Paul, Minn.

Preferred potassium salts include:

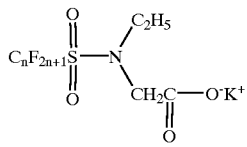

and $C_nF_{2n+1}SO_3^-K^+$, wherein n is about 3 to 18, as well as mixtures of these salts.

Useful potassium salts are made by following techniques disclosed in, for example, U.S. Pat. No. 2,809,990 (Brown). Examples of commercially available potassium salts include "Fluorad™ FC-127," "Fluorad™ FC-129" and "Fluorad™ FC-95 Fluorochemical Surfactant," from 3M. A useful ammonium salt is commercially available as "Fluorad™ FC-120 Fluorochemical Surfactant" from 3M.

2. Perfluorinated Radical Substituted Aliphatic Anionic Salts

Surfactants within this class are of the general formula described above, wherein:

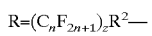

and wherein:

n is about 2 to 36, preferably 6 to 12;

$R^2$ is a branched or straight chain alkylene or aralkylene of about 2 to 36 carbon atoms, preferably 2 to 22 carbon atoms, optionally independently substituted in available positions with oxygen, nitrogen or sulfur atoms, which $R^2$ group is selected such that R comprises at least 7 carbon atoms; and z is about 1 to 3, preferably about 1 or 2.

Examples of commercially available salts of this class include "Zonyl™ FSA Fluorosurfactant" ($F(CF_2CF_2)_{3-8}CH_2CH_2SCH_2CH_2CO_2^-Li^+$) and "Zonyl™ FSE Fluorosurfactant" (a mixture of $F(CF_2CF_2)_{3-8}CH_2CH_2OP(O)(O^-NH_4^+)_2$ and $[F(CF_2CF_2)_{3-8}CH_2CH_2O]_2P(O)(O^-NH_4^+)$, from E. I. Du Pont de Nemours and Co.

3. Straight or Branched Chain Aliphatic Sulfates and Sulfonates

Surfactants within this class are of the general formula described above, wherein:

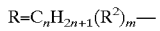

and wherein:

n is about 4 to 36, $R^2$ is a branched or straight chain alkyl or aralkyl of about 1 to 36 carbon atoms, preferably 1 to 22 carbon atoms, optionally independently substituted in available positions with oxygen, nitrogen or sulfur atoms;

m is 0 or 1, and

L is $SO_3^-$ or $SO_4^-$.

Examples of commercially available surfactants of this class include sodium dodecyl sulfate and sulfonates such as "Mackam™ CS"

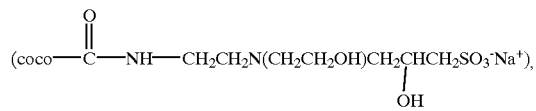

where "coco" means a mixture of alkyl chain lengths derived from coconut oil fatty acid residues, "Mackham™

CBS-50 Amphoteric" from The McIntyre Group Ltd., and "Hostastat HS-1" ($C_{10-18}H_{21-39}SO_3^-Na^+$), from Hoechst Celanese Corp.

4. Sulfates or Sulfonates of Polyethoxylated Derivatives of Straight or Branched Chain Aliphatic Alcohols and Carboxylic Acids Surfactants within this class are of the general formula described above, wherein:

$$R=C_nH_{2n+1}(CO)_pO(CH_2CH_2O)_yCH_2CH_2\text{—},$$

and wherein:
n is about 4–36,
p is 0 or 1 and
y is about 1–100, preferably 1–20; and
wherein
L is $SO_4^-$ or $SO_3^-$.

Examples of commercially available surfactants of this class include "Steol CA-460" ($C_{12}H_{25}O(CH_2CH_2O)_{12}SO_3^-Na^+$), from Stepan Co.

5. Alkylbenzene or Alkylnaphthalene Sulfonates and Sulfates

Surfactants within this class are of the general formula described above, wherein:

$$R=(C_nH_{2n+1})_qC_6H_{5-q}\text{—} \text{ or } (C_nH_{2n+1})_qC_{10}H_{7-q}\text{—}$$

and wherein:
n is about 4 to 36, preferably 8 to 22,
q is 1–3, preferably 1 or 2, and
L is $SO_3^-$ or $SO_4^-$.

Examples of commercially available surfactants of this class include "Rhodocal™ DS-10" (sodium laurylbenzene sulfonate) from Rhone-Poulenc Co., "Polystep™ A-16" ($C_{12}H_{23}\text{—}C_6H_6\text{—}SO^-_3Na^+$) and "Polystep™ A-15," from Stepan Co., and "Poly-Tergent™ 2EP" from Olin Corp.

6. Ethoxylated and Polyethoxylated Alkyl and Aralkyl Alcohol Carboxylates

Surfactants within this class are of the general formula described above, wherein:

$$R=(C_nH_{2n+1})_q(C_6H_{5-q})_mO(CH_2CH_2O)_yCH_2\text{—},$$

and wherein:
n is about 4 to 36, preferably 8 to 22,
m is 0 or 1, and
q is 1 or 2, preferably 1, and
y is about 1 to 100, preferably 1–20; and
wherein
L is $CO_2^-$.

Examples of commercially available surfactants of this class include "Sandopan LS-24 Carboxylated Surfactant" ($C_{12}H_{25}O(CH_2CH_2O)_{12}CH_2COO^-Na^+$) "Sandopan L8-HC Carboxylated Surfactant" and "Sandopan LA-8 Carboxylated Surfactant" ($C_{12}H_{25}O(CH_2CH_2O)_4CH_2COO^-Na^+$), from Sandoz Chemicals, Corp.

7. Glycinates

Surfactants within this class of the general formula described above, wherein:

$$R=R^2\text{—}C(O)N(R^3)CH_2\text{—},$$

wherein:
$R^2$ is a branched or straight chain alkyl of about 4 to 36 carbon atoms, preferably 8 to 22 carbon atoms, or an aralkyl group of about 7 to 36 carbon atoms, preferably 12 to 22 carbon atoms, which alkyl or aralkyl group is optionally independently substituted in available positions with oxygen, nitrogen or sulfur atoms; and $R^3$ is hydrogen or an alkyl group of about 1 to 10 carbon atoms which may be optionally independently substituted in available positions by oxygen, nitrogen or sulfur atoms;
and wherein L is $CO_2^-$.

Examples of preferred surfactants within this class are alkyl sarcosinates and alkyl glycinates. Examples of commercially available surfactants of this class include "Hampshire™ C-30," (coco-$C(O)N(CH_3)CH_2COO^-Na^+$) from Hampshire™ Chemical Co., and "Mackam™ Amphoteric" (dihydroxyethyl tallow glycinate) from the McIntyre Group, Ltd.

8. Sulfosuccinates

Surfactants within this class are of the general formula described above, wherein:

$$R= R^2\text{—}OC(O)\text{—}CH_2CH\text{—}C(O)OR^2,$$

and wherein:
$R^2$ is a branched or straight chain alkyl group of about 4 to 36 carbon atoms, preferably 8 to 22 carbon atoms, or an aralkyl group of about 7 to 36 carbon atoms, preferably 12 to 22 carbon atoms, which alkyl or aralkyl group may be independently substituted in available positions by oxygen, nitrogen and/or sulfur atoms; and
L is $SO_3^-$.

An example of a preferred surfactant of this class is dialkyl sulfosuccinate. Examples of commercially available surfactants of this class include "Aerosol™ OT Surface Active Agent" ($C_8H_{17}OC(O)\text{—}CH(SO_3^-Na^+)CH_2C(O)O\text{—}C_8H_{17}$) and "Aerosol™ TR Surface Active Agent" ($C_{13}H_{27}\text{—}OC(O)\text{—}CH(SO_3^-Na^+)CH_2C(O)O\text{—}C_{13}H_{27}$) from Cytec Industries.

9. Isethionate Derivatives

Surfactants within this class are of the general formula described above, wherein:

$$R=R^2\text{—}C(O)OCH_2CH_2\text{—}$$

and wherein $R^2$ is a branched or straight chain alkyl group of about 4 to 36 carbon atoms, preferably 8 to 22 carbon atoms, or an aralkyl group of about 7 to 36 carbon atoms, preferably 12 to 22 carbon atoms, which alkyl or aralkyl group is optionally independently substituted in available positions with oxygen, nitrogen or sulfur atoms; and
L is $SO^-_3$.

Examples of commercially available surfactants of this class include "Igepon™ AC-78" (coconut acid ester of sodium isethionate), from GAF Corp., New York, N.Y.

10. N-acyltaurine Derivatives

Surfactants within this class are of the general formula described above wherein:

$$R=R^2\text{—}C(O)N(R^3)CH_2CH_2\text{—}$$

and wherein $R^2$ is a branched or straight chain alkyl group of about 4 to 36 carbon atoms, preferably 8 to 22 carbon atoms, or an aralkyl group of about 7 to 36 carbon atoms, preferably 12 to 22 carbon atoms, which alkyl or aralkyl group is optionally independently substituted in available positions with oxygen, nitrogen or sulfur atoms;

$R^3$ is hydrogen or an alkyl group of about 1 to 10 carbon atoms which may be optionally independently substituted in available positions by oxygen, nitrogen or sulfur atoms; and $L=SO_3^-$.

Examples of commercially available surfactants of this class include "Igepon™ T-77" (sodium N-methyl-N-oleyltaurate), from GAF Corp.

11. Amphoteric Alkyl Carboxylates

Surfactants within this class are of the general formula described above, wherein:

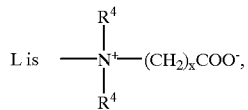

wherein $R^4$ is hydrogen, or an alkyl or alkylene carboxyl group of about 1 to 8 carbon atoms optionally substituted in available positions by nitrogen, oxygen or sulfur atoms, and x is 1 to 4; and wherein R is a branched or straight chain alkyl group of about 4 to 36 carbon atoms or an aralkyl group of about 7 to 36 carbon atoms which alkyl or aralkyl group is unsubstituted or independently substituted in available positions with oxygen, nitrogen or sulfur atoms.

Examples of preferred surfactants of this class are amphoteric propionates and alkyl and aryl betaines, optionally substituted with oxygen, nitrogen and/or sulfur atoms. Examples of commercially available surfactants of this class include "Tego™ Betain F-50" (coco-C(O)NH—$CH_2CH_2CH_2$—$N^+(CH_3)_2$—$CH_2COO^-$), from Goldschmidt Chemical Corp., "Mackam™ OB-30 Amphoteric" ($C_{18}H_{34}N^+(CH_3)_2CH_2COO^-$), "Mackam™ HV Amphoteric" ($C_{18}H_{34}C(O)NHCH_2CH_2CH_2N^+(CH_3)_2CH_2COO^-$) from the McIntyre Group, Ltd., "Miranol 2CIB" from Rhone-Poulenc, Co., and "Miratane™ AP-C" ($coco_2$-$N^+$H—$CH_2CH_2COO^-$) from Rhone-Poulenc Co.

12. Alkyl Phosphate Mono or di-esters

Surfactants within this class are of the general formula described above, wherein:

$$R=R^2O(CH_2CH_2O)_vCH_2CH_2—,$$

and wherein $R^2$ is a branched or straight chain alkyl group of about 4 to 36 carbon atoms, preferably 8 to 22 carbon atoms, or an aralkyl group of about 7 to 36 carbon atoms, preferably 12 to 22 carbon atoms, optionally independently substituted in available positions with oxygen, nitrogen or sulfur atoms;

v is 0–100, preferably 0–20; and

L is $PO_4^{-2}$ or $PO_4^-$.

Examples of commercially available surfactants of this class include "Rhodafac™ MC-470" (ethoxylated dodecyl alcohol phosphate ester, sodium salt) from Rhone-Poulenc, and "Sipostat 0012" ($C_{12}H_{25}OP(O)(O^-Na^+)_2$) and "Sipostat 0018" ($C_{18}H_{37}OP(O)(O^-Na^+)_2$) from Specialty Industrial Products, Inc., Spartanburg, S.C.

Applicants have discovered that the surfactants of he present invention can be utilized in concentrations which are effective to provide the coating composition with anti-fog properties, yet will not destroy the anti-reflective effects produced by the inorganic metal oxide. The anti-reflective property of the coating may be decreased by the surfactant, or by other additives, by one or both of two means. First, if too much surfactant is added, the void volume of the coating decreases thereby increasing the refractive index of the coating beyond that desired for maximum transmission of light. Secondly, the refractive index of the surfactant or additive can itself influence the refractive index of the coating. In general, the highest concentration of surfactant which will not adversely effect the anti-reflective property of the coating composition or the coating quality is preferred. Surfactants of lower refractive indices may be tolerated at higher concentrations on a weight basis. Rinsing or steeping the coated article in water may be desirable to remove excess surfactant or other additive. For typical concentrations of metal oxide (e.g., about 1 to 5 percent by weight) most surfactants comprise less than about 0.15 percent by weight of the coating composition, preferably less than 0.10 percent by weight, more preferably between about 0.003 and 0.05 percent by weight, and most preferably between about 0.01 and 0.05 percent by weight, in order to preserve the anti-reflective properties of the coating. It should be noted that with some surfactants a spotty coating is attained at concentrations in excess of what is needed to achieve the anti-fog property.

The surfactant may be applied as part of the metal oxide coating composition or may be applied, preferably in an aqueous or hydroalcoholic medium, as an "overcoat", i.e., can be applied as a separate coating solution over a previously deposited metal oxide coating. Preferably, the surfactant is added directly to the metal oxide sol coating composition to simplify the coating process and to minimize any risk of scratching the metal oxide layer.

Other Additives

Many of the surfactants of the present invention not only impart anti-fog properties to the film but also lower the surface tension of aqueous coating solutions such that the solution uniformly wets and coats the article. In some instances, however, in order to ensure uniform coating of the article from an aqueous or hydroalcoholic solution it may be beneficial to add a wetting agent, which is typically a surfactant, including many of the surfactants described herein, as well as surfactants that do not impart durable anti-fog properties. Examples of useful wetting agents include polyethoxylated alkyl alcohols (e.g. "Brij 30," and "Brij 35," commercially available from ICI Americas, Inc., and "Tergitol™ TMN-6T Specialty Surfactant," commercially available from Union Carbide Chemical and Plastics Co.), polyethoxylated alkylphenols (e.g., "Triton™ X-100" from Union Carbide Chemical and Plastics Co., "Iconol NP-70" from BASF Corp.) and polyethylene glycol/polypropylene glycol block copolymer (commercially available as "Tetronic™ 1502 Block Copolymer Surfactant," "Tetronic™ 908 Block Copolymer Surfactant" and "Pluronic™ F38 Block Copolymer Surfactant," all from BASF, Corp.) Of course, any added wetting agent must be included at a level which will not destroy the anti-reflective or anti-fog properties of the coating. Generally the wetting agent is used in amounts of up to about 0.10 weight percent of the coating composition depending on the amount of inorganic metal oxide. Preferably the wetting agent is present in amounts less than 0.05, more preferably less than 0.03, weight percent of the coating composition. Alternatively, lower alcohols ($C_1$ to $C_8$) in the coating solution have proven useful in improving wetting.

The coating compositions of the present invention may also include a coupling agent capable of covalently bonding the surfactant to the metal oxide. Some coupling agents are capable of reacting with specific functional groups on the surface of the article to be coated. Consequently, the coupling agent may be capable of promoting adhesion of the coating composition to the substrate. The coupling agent has at least two reactive functionalities. One reactive functionality is capable of covalently bonding to the metal oxide and the second is capable of covalently bonding to the surfactant. For example, reactive functionalities such as amino, hydroxyl, mercaptan, acrylate and methacrylate groups present on one compound (the surfactant, coupling agent, or the metal oxide) can react with complementary reactive functionalities, such as oxirane, chloro-, bromo-, iodo-, alkyl, aziridine, anhydride, acrylate, methacrylate, or isocyanato groups, present on the other compound (coupling agent or surfactant). More than one coupling agent may be used. For example, two types of coupling agents which are capable of covalently bonding to each other may be employed where one coupling agent is capable of covalently bonding to the metal oxide and the other is capable of covalently bonding to the surfactant.

Useful silane coupling agents include those with the following formula:

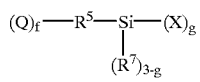

wherein:
R$^5$ is a substituted or unsubstituted divalent hydrocarbon bridging group of about 1 to 20 carbon atoms, optionally including in the backbone 1 to 5 moieties selected from the group consisting of —O—, —C(O)—, —S—, —SO$_2$— and —NR$^6$— groups, and optionally substituted on the backbone by —OH, —SH, or —NR$^6$—$_2$ wherein R$^6$ is hydrogen, acetyl, or a hydrocarbon group of 1 to 6 carbon atoms;

X is —OR$^8$ where R$^8$ is an alkyl, aryl, heteroaryl, or aralkyl group of 1 to 8 carbon atoms, preferably methyl or ethyl; or —N=C(R$^9$)$_2$, wherein R$^9$ is independently an alkyl, aryl or aralkyl group of 1 to 8 carbon atoms;

R$^7$ is independently an alkyl, aryl, aralkyl or alkoxy group of 1 to 8 carbon atoms optionally substituted in available positions by oxygen, nitrogen and/or sulfur atoms;

f is 0, 1, or 2;

g is 2 or 3; and

Q is a reactive functional group capable of reacting with complementary functionalities on the surface of the substrate or the surfactant. Examples of Q include amino; hydroxyl; mercaptan; oxirane; chloro-, iodo-, and bromo-alkyl; aziridine; cyclic carboxylic anhydride; acrylate; methacrylate; acrylamide, azide, and isocyanato groups. It should be understood that when present in the coating compositions of the invention (particularly with base stabilized sols) the coupling agents will hydrolyze, in which case one or more of the "X" or "OR$^2$" groups will be converted to a silanol or silanolate.

Preferred silanes have the structure:

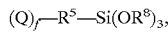

wherein Q is preferably a primary or secondary epoxy or amino group and R$^5$ and R$^8$ are as described above.

Additional information on ambifunctional silane coupling agents may be found in European Patent Application No. 0,372,756 A2, incorporated herein by reference. Alternatively the coupling agent can be a titanate or zirconate compound, such as "Tyzor™ Titanate," commercially available from Du Pont.

The amount of coupling agent included in the coating composition should be limited in order to prevent destruction of the anti-reflective or anti-fog properties of the coating. The optimal amount of coupling agent is easily determined experimentally and is a function of the coupling agent's identity, molecular weight and refractive index. The coupling agent(s), when present, are typically added to the composition at levels of 0.1 to 20 percent by weight of the metal oxide concentration, and more preferably about 1 to 10 percent by weight of the metal oxide. Tetraalkoxy coupling agents, such as tetraethylorthosilicate (TEOS) and oligomeric forms such as alkyl silicates (e.g. poly(diethoxy siloxane)), may also be useful to improve binding between metal oxide particles.

Additional materials capable of bonding with the metal oxide and improving the durability of the anti-fog coatings of this invention include silane agents. Preferred silane agents are particular anionic silanes (described below) which are capable of themselves providing anti-fog properties to substrates or articles coated therewith. Such preferred anionic silanes are described in commonly assigned copending United States patent application, Attorney's Docket number 51197USA8A, filed upon the same date as this application U.S. Ser. No. 08/354,343, U.S. Pat. No. 5,595, 186 and incorporated herein by reference. The term anionic silane as used herein describes organofunctional silicon containing compounds capable of hydrolyzing to organosilanol with subsequent condensation to organofunctional siloxane oligomers.

The preferred anionic silane compounds useful in the solutions and compositions of the present invention have the following general structure:

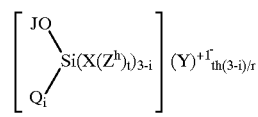

wherein:
Q is selected from the group consisting of hydroxyl, alkyl groups containing from 1 to about 4 carbon atoms, and alkoxy groups containing from 1 to about 4 carbon atoms;

J is selected from cations derived from the group consisting of hydrogen, alkali metals and organic cations of strong bases having an average molecular weight of less than about 150 and a pKa of greater than about 11;

X is an organic linking group;

Z is selected from the group consisting of —OSO$_2$O$^-$, —SO$_2$O$^-$, —CO$_2^-$, (—O)$_2$P(O)O$^-$—P(O)(O$^-$)$_2$, —OP(O)(O$^-$)$_2$, —P(O$^-$)$_2$ and —OP(O$^-$)$_2$;

Y is selected from cations derived from the group consisting of hydrogen, alkali metals, alkali earth metals, organic cations of weak bases having an average molecular weight of less than about 200 and a pKa of about 8 to 11 (e.g., HN$^+$(CH$_2$CH$_2$CH$_2$OH)$_3$ and H$_2$N$^+$(CH$_2$CH$_2$OH)$_2$), organic cations of strong bases having an average molecular weight of less than about 150 and a pKa of greater than about 11, substituted and unsubstituted guanidines, and quaternary ammonium cations (e.g. N$^+$(CH$_3$)$_4$, N$^+$(CH$_2$CH$_3$)$_4$ and N$^+$H$_4$); provided that J is hydrogen when Y is selected from cations derived from hydrogen, alkaline earth metals and said weak organic bases;

r is equal to the valence of Y and is 1 to 3;
h is 1 or 2;
i is 1 or 2; and
t is 1 to 3.

Preferably Z is sulfonate ($SO_2O^-$) or phosphonate (—P(O)($O^-$)$_2$) or carboxylate ($CO_2^-$), more preferably sulfonate and phosphonate, and the preferred anionic silane is an organosilanol, such as the sulfonato-organosilanols disclosed in U.S. Pat. No. 4,235,638 to Beck, incorporated herein by reference. Alternatively, the anionic silane may be one of those disclosed in U.S. Pat. Nos. 3,816,184; 4,344,860; or 4,370,255; all of which are incorporated herein by reference. The organic linking group X, is preferably selected from alkylene groups, cycloalkylene groups, hydroxy-substituted alkylene groups, hydroxy-substituted mono-oxa alkylene groups, divalent hydrocarbon groups having mono-oxa backbone substitution, divalent hydrocarbon groups having mono-thia backbone substitution, divalent hydrocarbon groups having monooxa-thia backbone substitution, divalent hydrocarbon groups having dioxathia backbone substitution, arylene groups, arylalkylene groups, alkylarylene groups, and alkylarylene groups, all of which groups may be substituted by N, O and/or S atoms and all of which X groups comprise from about 1 to 20 carbon atoms, preferably from about 1 to 6 carbon atoms. Most preferably X is selected from alkylene groups, hydroxy-substituted alkylene groups and hydroxy-substituted mono-oxa alkylene groups.

In order to ensure optimum hydrophilicity and maximize the durability of the coating, the preferred anionic organosilanol preferably has a relatively high percentage of oxygen on a weight percentage basis. Preferably, the weight percent oxygen is at least about 30%, more preferably at least about 40%, and most preferably in the range of about 45 to 55%. In general, the weight percent silicon in these compounds is no greater than about 15%. Each of these percentages is based on the weight of the compound in the water-free acid form. Aqueous or hydroalcoholic solutions of the organosilanol-sulfonic acids (i.e. Z is $SO_3^-$ and Y is hydrogen) are acidic generally having a pH of less than about 5 while the organo-silanolate-sulfonate salts are basic and generally have a pH of greater than about 9.0. In order to prevent destabilization of the preferred base stabilized metal oxide sols the organo-silanolate-sulfonate salt form is preferred.

The anionic organosilanol may be applied as part of the metal oxide and/or surfactant containing coating composition or may be applied as an "overcoat", i.e. can be applied as a separate coating solution applied over a previously deposited metal oxide and/or surfactant containing coating. Preferably, the anionic organo-silanol is added directly to the metal oxide sol and surfactant-containing coating composition to simplify the coating process and to minimize any risk of scratching the metal oxide layer.

The preferred anionic organosilanols are most conveniently applied from an aqueous or hydroalcoholic solution and therefore may be partially or completely hydrolyzed to the silanol/silanolate form and may include oligomeric siloxane forms of the anionic organosilanol. The level of organosilanol must be kept relatively low with respect to the metal oxide concentration in order to prevent reduction in the anti-reflective property. The anti-reflective property may be decreased by one or both of two means. Firstly, if too much organosilanol is added the porosity (void volume) of the coating decreases, thereby increasing the refractive index of the coating beyond that desired for maximum transmission of light. Secondly the refractive index of the silane itself might influence the refractive index of the coating if the amount of silane becomes excessive. In general, the highest level of anionic silane which will not adversely affect the anti-reflective property or coating quality is preferred. The anionic silanes are preferably added to the coating composition at a concentration of about 5 to 50% by weight of the metal oxide. More preferably the anionic silanes are added to the coating composition at a concentration of about 10 to 30% by weight of the metal oxide, in order to preserve the anti-reflective properties of the coating.

The coating composition may optionally contain a polymeric binder to improve scratch resistance and/or adhesion of the coating composition to the substrate. Useful polymeric binders are preferably water soluble or water swellable and include polymers comprised of ethenically unsaturated monomer(s), such as polyvinyl alcohol, polyvinylpyrrolidone, polyvinyl acetate, polyacrylates and methacrylates and polyurethanes; polyesters; natural polymers such as starch, gelatin, gums, celluloses, dextran, proteins and the like; and derivatives (ionic and non-ionic) and copolymers based on any of the polymers listed above. Furthermore, polymers comprising alkoxysilane functionalities may also be useful. The coating composition can contain up to about 5 weight percent of the polymeric binder based on the weight of the inorganic metal oxide. Useful amounts of polymeric binder are generally in the range of about 0.05 to 5 weight percent by weight to improve scratch resistance and coating adhesion.

It is also possible to apply a primer coating to improve adhesion of the coating to the substrate. A particularly preferred primer material is polyvinylidene chloride (PVDC).

Articles

Substrates to which the coating compositions of the invention can be applied are preferably transparent or translucent to visible light. Preferred substrates are made of polyester (e.g., polyethylene terephthalate, polybutyleneterephthalate), polycarbonate, allyldiglycolcarbonate, polyacrylates, such as polymethylmethacrylate, polystyrene, polysulfone, polyethersulfone, cellulose acetate butyrate, glass and the like, including blends and laminates thereof. Typically the substrate is in the form of a film, sheet, panel or pane of material and is part of an article such as ophthalmic lenses, architectural glazings, decorative glass frames, motor vehicle windows and windshields, and protective eye wear, such as surgical masks and face shields. The coatings may if desired, cover only a portion of the article, e.g., only the section immediately adjacent the eyes in a face shield may be coated. The substrate may be flat, curved or shaped. The article to be coated may be produced by blowing, casting, extrusion, or injection molding.

Articles such as disposable surgical face masks and face shields which are coated with the anti-reflective, anti-fog compositions of this invention are preferably stored in single use packages which reduce environmental exposure and contamination which can result in decreased anti-fog properties. Reusable articles are preferably used in combination with a package that protects or completely seals the product from environmental exposure when not in use. The material used to form the packages should be comprised of a non-contaminating material. It has been found that certain materials can result in partial or total elimination of the anti-fog properties. While not being bound by any theory, it is currently believed that materials which contain plasticizers, catalysts, and other low molecular weight materials which can volatilize on aging are sorbed into the coating and result in a decrease in the anti-fog property. For example, packaging materials such as polyurethane foams, plasticized polyvinylchloride and low density polyethylene have been found to significantly reduce the anti-fog properties of the articles of the present invention, especially when in direct contact with the coating. Currently preferred packaging materials include paper and bleached paper products, such as bleached white bond paper, cardboard, and clay-coated solid white bleached sulfate boxboard, and/or films or laminates made from polyester, high density polyethylene, or polystyrene.

Process

The compositions of the present invention are preferably coated on the article using conventional techniques, such as bar, roll, curtain, rotogravure, spray, or dip coating techniques. The preferred methods include bar and roll coating or air knife coating to adjust thickness. In order to ensure uniform coating and wetting of the film, it is convenient to oxidize the substrate surface prior to coating using corona discharge or flame treatment methods. These methods may also improve adhesion of the coating to the substrate. Other methods capable of increasing the surface energy of the article include the use of primers such as thin coatings of polyvinylidene chloride (PVDC). The coatings of the present invention are preferably applied in uniform average thicknesses varying by less than about 200 Å, and more preferably by less than 100 Å, in order to avoid visible color variations in the coating. The optimal average dry coating thickness is dependent upon the particular coating composition, but in general the average thickness of the coating is between 500 and 2500 Å, preferably 750 to 2000 Å, and more preferably 1000 to 1500 Å, as measured using an ellipsometer such as a Gaertner Scientific corp. Model No. L115C. Above and below this range, the anti-reflective properties of the coating may be significantly diminished. It should be noted, however, that while the average coating thickness is preferably uniform, the actual coating thickness can vary considerably from one particular point on the coating to another. This variation in thickness, when correlated over a visibly distinct region, may actually be beneficial by contributing to the broad band anti-reflective properties of the coating.

The coatings of the present invention are preferably coated on both sides of the substrate. Alternatively, the coatings of the present invention may be coated on one side of the substrate. The opposite side of the substrate may be:

a. uncoated,
b. coated with a conventional surfactant or polymeric anti-fogging composition such as that disclosed in U.S. Pat. Nos. 2,803,552; 3,075,228; 3,819,522; 4,467,073; or 4,944,294 (all of which are incorporated herein by reference), or
c. coated with an anti-reflective composition, such as that disclosed in U.S. Pat. No. 4,816,333, or the multiple layered coating described by J. D. Masso in "Evaluation of Scratch Resistant and Anti-reflective Coatings for Plastic Lenses," (supra), both of which are incorporated herein by reference. Preferably, the coating surface should face the direction of higher humidity, e.g., on a face shield the side having the anti-fog coating should face the wearer.

Once coated, the article is typically dried at temperatures of between 20 and 150° C. in a recirculating oven. The temperature may be increased further to speed the drying process, but care must be exercised to avoid degradation of the substrate. The preferred coating compositions are preferably dried at between 50 and 120° C. and most preferably between 100 and 110° C. After the coating is applied to the substrate and dried, it comprises preferably from about 85 to 99.7 percent by weight (more preferably from about 88 to 95 percent by weight) metal oxide, about 0.25 to 5 percent by weight (more preferably from about 0.2 to 2 percent by weight) surfactant, up to about 25 percent by weight (more preferably from about 5 to 15 percent by weight) coupling agent and up to about 5 percent by weight (preferably up to about 2 percent by weight) wetting agent.

When the coating compositions of the invention are applied to substrates to provide anti-reflection properties, glare is reduced by increasing the light transmission of the coated substrate. Preferably, the coated substrate exhibits an increase in transmission of light of at least 3 percentage points and up to as much as 10 percentage points or more, when compared to an uncoated substrate, at 550 mm (e.g., the wavelength at which the human eye displays peak photo-optic response). The percent transmission is dependent upon the angle of incidence and the wavelength of light and is determined using ASTM test method D1003-92, entitled "Haze and Luminous Transmittance of Transparent Plastics," incorporated herein by reference. Preferably, the coated substrates display an increase in percent transmission of greater than 3 percent, more preferably greater than 5 percent, and most preferably greater than 8 percent when compared with an uncoated substrate, using 550 nm light. When the desired usage involves significant "off-axis" (i.e., non-normal) viewing or unwanted reflections, gains in visibility may be greater especially where the reflections approach or exceed in brightness the object in view.

The coating compositions of the invention, as discussed hereinabove, provide anti-fog as well as anti-reflective properties to surfaces coated therewith. The anti-fog property is demonstrated by the tendency of the coatings to resist the formation of water droplets which tend to significantly reduce the clarity or transparency of the coated substrate. Water vapor from, for example, human breathing, tends to condense upon the coated substrate in the form of a thin uniform water film, rather than as water droplets. Such a uniform film does not significantly reduce the transparency of the substrate. For example, using the "Wetting Test" described in the Examples, when a 3 microliter drop of water is placed on the surface of a substrate coated with the coating composition of the invention, the drop spreads to an initial diameter of at least 6 mm, preferably at least 7 mm, and most preferably at least 8 mm.

The coating compositions of the present invention are durable and shelf stable, e.g., they do not deteriorate significantly when allowed to be exposed at 23° C. and 50% relative humidity for up to sixteen weeks. Preferred coatings when exposed at 30° C. and 60% relative humidity in a recirculated environmental chamber (the circulation rate= 1.67 vol./min.) for at least fourteen days, and, more preferably, at least twenty-one days, and most preferably twenty-eight days, and tested according to the "Wetting Test" described in the examples, have a 3 microliter drop diameter of at least 4 mm, and more preferably at least 5 mm.

EXAMPLES

The surfactants present in the anti-fog/anti-reflective compositions of Examples 1 through 63 and Comparative Examples A through AH are described in Table 1.

TABLE 1

| Ex. No. | Surfactant Class | Type - chemical description | Trade Name | Source/Address |
|---|---|---|---|---|
| 1, 20, 42 | Perfluorinated radical substituted aliphatic anionic salts | anionic - fluorochemical surfactant | Zonyl ™ FSA Fluoro-Surfactant | E. I. Du Pont de Nemours & Co., Chemicals Dept., Wilmington, DE; |
| 2, 19, 41 | Sulfosuccinates | anionic - dioctyl ester of sodium sulfosuccinic acid | Aerosol ™ OT Surface Active Agent | Cytec Industries, Process Chemicals, Unit of American Cyanamid, Weat Paterson, NJ |
| 3, 23, 40 | Alkylbenzene sulfonates and sulfates | anionic - sodium branched alkyl ($C_{12}$) benzene sulfonate | Polystep ™ A-16 | Stepan Company, Northfield, IL |
| 4, 21 | Alkylbenzene sulfonates and sulfates | anionic - sodium dodecyl benzene sulfonate | Rhodocal ™ DS-10 | Rhone-Poulenc, Surfactant & Specialty Division, Cranberry, NJ |
| 5 | Ethoxylated and polyethoxylated alkyl or aralkyl alcohol carboxylates | anionic - alkyl ($C_{12}$–$C_{15}$) (ethoxylated) carboxylate | Sandopan LS-24 Carboxy-lated Surfactant | Sandoz Chemicals Corp., Charlotte, NC |
| 6, 15 | N-acyltaurine derivatives | anionic - alkyl ($C_{18}$) sulfoamide sodium N-methyl-N-oleyl taurate | Igepon ™ T-77 | GAF, New York, NY |
| 7 | Amophoteric alkyl carboxylates | amphoteric-cocamidopropyl betaine | Tego ™ Betaine F-50 | Goldschmidt Chemical Corp., Hopewell, VA |
| 8, 22, 53–60, Comp. Z–AC | Perfluoroaliphatic anionic surfactants | anionic - ammonium perfluoroalkyl sulfonate | Fluorad ™ FC-120 Fluoro-chemical Surfactant | 3M Company, Specialty Chemical Producta Division, Maplewood, MN |
| 9, 11, 26, 33 | Perfluoroaliphatic anionic surfactants | anionic $C_{10}F_{21}SO_3Li$ | | Made as described in U.S. Pat. No. 2,732,398 (Brice et al.) Example 2 |
| 10, 25 | Perfluoroaliphatic anionic surfactants | anionic $C_8F_{17}SO_3Li$ | | Made as described in U.S. Pat. No. 2,732,398 (Brice et al.) Example 2 |
| 12, 31 | Polyethoxylated derivatives of straight or branched chain aliphatic sulfates | anionic - polyethoxylated alkyl ($C_{12}$) ether sulfate, ammonium salt | Steol CA-460 | Stepan Company, Northfield, IL |
| 13 | Perfluorinated radical substituted aliphatic anionic salts | anionic - fluorochemical surfactant | Zony ™ FSE Fluoro-Surfactant | E. I. Du Pont de Nemours & Co., Chemicals Dept., Wilmington, DE |
| 14 | Isetnionate derivatives | anionic - alkyl ($C_{13}$) sulfoester ($SO_3^-Na^+$) | Igepon ™ AC-78 | obtained from GAF, New York, NY |
| 16 | Ethoxylated and polyethoxylated alkyl or aralkyl alcohol carboxylates | anionic - polyethoxylated alkyl ($C_{10}$–$C_{16}$) carboxylates | Sandopan L8-HC Carboxy-lated Surfactant | Sandoz Chemicals Corp., Charlotte, NC |
| 17 | Straight or branched chain aliphatic sulfates and sulfonates | anionic - aliphatic sulfates | Hostastat HS-1 | Hoechst Celanese Corp., Colorants & Surfactants, Charlotte, NC |
| 18 | Glycinates | anionic sodium cocoyl sarcosinate ($CO_2^-Na^+$) | Hampshire ™ Hamposyl C-30 | Hampshire Chemical Lexington, MA |
| 24 | Alkylbenzene sulfonates and sulfates | anionic - sodium linear alkyl ($C_{12}$) benzene sulfonate | Polystep ™ A-15 | Stepan Company, Northflied, IL |
| 27 | Glycinates | amphoteric - dihydroxyethyl tallow glycinate | Mackam ™ TM Amphoteric | The McIntyre Group Ltd., University Park, IL |
| 28 | Sulfosuccinates | anionic - alkyl ($C_{13}$) sulfosuccinates | Aerosol ™ TR Surface Active Agent | Cytec Industries, Process Chemicals, Unit of American Cyanamid, West Paterson, NJ |
| 29 | Amphoteric alkyl carboxylates | amphoteric - oleyl betaine | Mackam ™ OB-30 Amphoteric | The McIntyre Group Ltd., University Park, IL |

TABLE 1-continued

| Ex. No. | Surfactant Class | Type - chemical description | Trade Name | Source/Address |
|---|---|---|---|---|
| 30 | Amphoteric alkyl carboxylates | amphoteric - dicarboxylic coconut imidazoline derivative, sodium salt | Miranol ™ 2CIB | Rhone-Poulenc, Surfactant & Specialty Division, Cranberry, NJ |
| 32 | Alkyl phosphate mono- or di- esters | alkyl ($C_{18}$) phosphate ester ($PO_4^- Na_2^+$) | Sipostat 0018 | Specialty Industrial Producis Inc., Spartanburg, SC |
| 34, 50, 51, 52, Comp. U–Y | Perfluoroaliphatic anionic surfactants | anionic - potassium perfluoroalkyl sulfonate | Fluorad ™ FC-95 Fluorochemical Surfactant | 3M Company, Specialty Chemical Products Division, Maplewood, MN |
| 35 | Straight or branched chain aliphatic sulfates and sulfonates | amphoteric - cocamidopropyl hydroxysultaine | Mackam ™ CBS-50 Amphoteric | The McIntyre Group Ltd., University Park, IL |
| 36 | Amphoteric alkyl carboxylates | amphoteric - N-coco-β-aminopropionic acid | Mirataine ™ AP-C | Rhone-Poulenc, Surfactant & Specialty Division, Cranberry, NJ |
| 37 | Alkylbenzene sulfonates and sulfates | anionic - sodium salt of dodecyl diphenyl ether disulfonate derived from propylene tetramer | Poly-Tergent ™ 2EP | Olin Corp., Stamford, CT |
| 38 | Amphoteric alkyl carboxylates | amphoteric - oleamido betaine | Mackam ™ HV Amphoteric | The McIntyre Group Ltd., University Park, IL |
| 39 | Alkyl phosphate mono- or di- esters | ethoxylated dodecyl alcohol phosphate ester, sodium salt ($PO^- Na^+$) | Rhodafac ™ MC-470 | Rhone-Poulenc, Surfactant & Specialty Division, Cranberry, NJ |
| 43, 45 | Perfluoroaliphatic anionic surfactants | anionic - potassium sait of a perfluoro-aliphatic sulfonamido carboxylate | Fluorad ™ FC-129 Fluoro-chemical Surfactant | 3M Company, Specialty Chemical Products Division, Maplewood, MN |
| 44, 46 | Perfluoroaliphatic anionic surfactants | anionic- potassium salt of a perfluoro-aliphatic sulfonamido carboxylate | Fluorad ™ FC-127 Fluoro-chemical Surfactant | 3M Company, Specialty Chemical Products Division, Maplewood, MN |
| 47, 48 | Perfluoroaliphatic anionic surfactants | anionic - $C_4F_9PO_3(Li)_2$ | | U.S. Pat. No. 2,732,398 (Brice et al.) Example 2 and U.S. Pat. No. 2,109,990 (Brown) |
| 49 | Perfluoroaliphatic anionic surfactants | anionic - $C_3F_7CO_2Li$ | | U.S, Pat. No. 2,732,398 (Brice et al.) Example 2 and U.S. Pat. No. 2,809,990 (Brown) |
| 61, Comp. AD, AF, AH | Perfluoro-aliphatic anionic acid | anionic - $C_4F_9SO_3H$ | | U.S. Pat. No. 2,732,398 (Brice et al.) Example 2 and U.S. Pat. No. 2,809,990 (Brown) |
| 62, 63, Comp. AE, AG | Perfluoroaliphatic anionic surfactants | anionic - an ammonium salt of an anionic perfluoro-aliphatic radical containing sulfonate | Fluorad ™ Fluorochemical Surfactant | 3M Company, Specialty Chemical Products Division, Maplewood, MN |
| Comp. A | Polyethoxylated alkyl phenol | nonionic - polyethoxylated octyl phenols | Triton ™ X-100 | Union Carbide Chemical & Plastics Co., Industrial Chemicals Division, Danbury, CT |
| Comp. B | Polyethoxylated alkyl alcohol | nonionic - polyoxyethylene (23)lauryl ether | Brij ™ 35 | ICI Americas Inc., Wilmington, DE |
| Comp. C | Block copolymers of polyethylene oxide and polypropylene oxide | nonionic - block copolymer of ethylene oxide and propylene oxide, ethylene diamine started (PEG/PPG/PEG block copolymer) | Tetronic ™ 1502 Block Copolymer Surfactant | BASF Corp., Performance Chemicals, Parsippany, NJ |
| Comp. D | Polyethoxylated alkyl alcohol | nonionic - polyoxyethylene (4) lauryl ether | Brij ™ 30 | ICI Americas Inc., Wilmington, DE |

TABLE 1-continued

| Ex. No. | Surfactant Class | Type - chemical description | Trade Name | Source/Address |
|---|---|---|---|---|
| Comp. E | Block copolymers of polyethylene oxide and polypropylene oxide | nonionic - PEG/PPG/PEG block copolymer | Pluronic ™ F38 Block Copolymer Surfactant | BASF Corp. Performance Chemicals, Parsippany, NJ |
| Comp. F | Polyethoxylated alkyl phenol | nonionic - polyethoxylated nonyl phenol | Iconol NP-70 | BASF Corp. Performance Chemicals, Parsippany, NJ |
| Comp. G | Block copolymers of polyethylene oxide and polypropylene oxide | nonionic - PEG/PPG/PEG block copolymer | Tetronic ™ 908 Block Copolymer Surfactant | BASF Corp., Performance Chemicals, Parsippany, NJ |
| Comp. H | Perfluorinated radical containing polyethoxylated alcohol | nonionic - fluorochemical surfactant | Zonyl ™ FSN Fluoro-Surfactant | E. I. Du Pont de Nemours & Co., Chemicals Dept., Wilmington, DE |
| Comp. I | Polyethoxylated alkyl alcohol | nonionic - $C_{11}$–$C_{15}$ secondary alcohol ethoxylate | Tergitol ™ 15-S-40 Specialty Surfactant | Union Carbide Chemical & Plastics Co., Danbury, CT |
| Comp. J | Amine oxide | nonionic - lauryl dimethylamine oxide | Rhodsinox ™ LO | Rhone-Poulenc, Surfactant & Specialty Division, Cranberry, NJ |
| Comp. K | Polyethoxylated alkyl alcohol | nonionic - ethoxylated trimethylnonanol | Tergitol ™ TMN-6 Specialty Surfactant | Union Carbide Chemical & Plastics Co., Danbury, CT |
| Comp. L | | ammonium xylene sulfonate | | Reutgers-Neese Chemical Co., State College, PA |
| Comp. M | Alkyl carboxylate | lithium stearate | | See Preparation in Comparative Examples M–N |
| Comp. N | Alkyl carboxylate | sodium stearate NF | | Witco, Organics Division, New York, NY |
| Comp. O, R | Perfluoroaliphatic nonionics | nonionic - perfluoroaliphatic radical containing sulfonamide | Fluorad ™ FC-170 Fluorochemical Surfactant | 3M Company, Specialty Chemical Products Division, Maplewood, MN |
| Comp. P, S | Perfluoroaliphatic nonionics | nonionic - perfluoroaliphatic radical containing sulfonamide | Fluorad ™ FCA-431 Fluoro-chemical Surfactant | 3M Company, Specialty Chemical Products Division, Maplewood, MN |
| Comp. Q, T | Perfluoroaliphatic nonionics | nonionic - perfluoroaliphatic radical containing sulfonamide | Fluorad ™ FC-171 Fluoro-chemical Surfactant | 3M Company, Specialty Chemical Products Division, Maplewood, MN |

Examples 1–11 and Comparative Examples A–C

The anti-fog/anti-reflective compositions of Examples 1 through 11 and the comparative anti-reflective compositions of Comparative Examples A through C were prepared by adding the surfactants described in Table 1 in the amounts given in Table 2 to a dispersion containing 1.75 weight percent silica prepared by dilution of "Remasol SP-30 Sodium Stabilized Silica Sol" (supplied as a 30 percent solution, particle size 70 Å, pH 10) commercially available from Remet Corp., Chadwicks, N.Y., in deionized water. A glycidoxypropyltrimethoxysilane (GPS) coupling agent, commercially available as "A-187" from Union Carbide Chemical & Plastics Company, Danbury, Conn., was added to the dispersion of Example 11 at a concentration of 0.17 percent by weight. The compositions were coated on both sides of a 0.18 mm (7 mil) thick flame treated polyethylene terephthalate (PET) film using a roll coater with an air knife to adjust thickness of the dried coating to a violet to slightly blue hue when viewed by reflected light. (approximately 1,000 to 1,200 Å). The coated film was immediately passed into a forced air dryer at a temperature of 77° C. The dwell time in the oven was less than 2 minutes. The samples were evaluated for fog resistance the day the coated film samples were made ("initial fog") and again after aging 12 days in storage but with the surfaces exposed to ambient conditions of approximately 23° C. and 50 percent relative humidity. Fogging was evaluated by breathing directly on the film with the film held approximately 2.5 cm from the mouth. Initial fog was determined subjectively as "excellent," "good," "okay," and "poor" depending on the relative ability to see through the film after breathing upon it. The following numerical ratings were used for the 12-day evaluation: "1" means the coated film fogs like the uncoated film; "2" means the coated film fogs after 1–2 consecutive breaths; "3" means the coated film had a light fog after 3 consecutive breaths; "4" means the coated film had a very light fog after 4 consecutive direct breaths; and "5" means the coated film resisted fogging after 5 consecutive direct breaths. The results are reported in Table 2. All of the coated films, when visually compared to uncoated film and held up to a textured beige surface, were significantly more transparent and anti-reflective.

TABLE 2

| Example Number | Surfactant Concentration (weight %) | Initial Fog | Fog After 12 days Aging |
| --- | --- | --- | --- |
| Comp. A | 0.150 | good | 2 |
| Comp. B | 0.014 | good | 2 |
| Comp. C | 0.015 | poor | 2 |
| 1 | 0.015 | excellent | 5 |
| 2 | 0.010 | excellent | 4 |
| 3 | 0.015 | good | 4 |
| 4 | 0.015 | good | 5 |
| 5 | 0.018 | good | 5 |
| 6 | 0.015 | good | 4 |
| 7 | 0.014 | good | 4 |
| 8 | 0.015 | okay | 5 |
| 9 | 0.015 | good | 5 |
| 10 | 0.035 | good | 5 |
| 11 | 0.040 | good | 5 |

Discussion of Results: The films which were coated with compositions containing the surfactants in Comparative Example A and B were resistant to fogging 12 days. The film which was coated with a composition containing the surfactant used in Comparative Example C was easily fogged initially and after aging. The eleven films which were coated with compositions containing the variety of surfactants in Examples 1–11 had good to excellent resistance to fogging initially and after aging for 12 days.

Examples 12–13 and Comparative Examples D–I

The anti-fog/anti-reflective compositions of Examples 12 and 13 and the comparative anti-reflective compositions of Comparative Examples D through I were prepared by adding the types of surfactants described in Table 1 in the amounts given in Table 3 to a dispersion containing 1.25 weight percent silica prepared by dilution of "Nalco 2326 Colloidal Silica as $SiO_2$" (supplied at 15 weight percent, particle size 50 angstroms), commercially available from Nalco Chemical Company, Naperville, Ill., in deionized water. A silane coupling agent, glycidoxypropyltrimethoxysilane (GPS), commercially available as "A-187" from Union Carbide Chemical & Plastics Company, was also added to the composition of Comparative Examples D–I and Example 12. Another silane coupling agent commercially available as "A1230," a proprietary nonionic silane dispersing agent from Union Carbide Chemical & Plastics Company, was added to the composition of Example 13. The amounts of silane coupling agents are described in Table 3. The compositions were allowed to sit for approximately 1 hour prior to coating. The compositions were coated by hand on one side only of a 0.18 mm (7 mil) thick PET film using a number 8 Meyer bar. The coated films were dried in an oven at 85° C. for approximately 5 minutes. The coated side of the film was evaluated for fogging approximately 24 hours after coating. Fogging was determined using the fogging test described for 12 day fog in Examples 1–11. The results are reported in Table 3.

TABLE 3

| Example Number | Silane Concentration (Weight %) | Surfactant Concentration (Weight %) | Initial Fog |
| --- | --- | --- | --- |
| Comp. D | 0.15 | 0.150 | 1 |
| Comp. E | 0.12 | 0.120 | 1 |
| Comp. F | 0.12 | 0.120 | 2 |
| Comp. G | 0.10 | 0.120 | 1 |
| Comp. H | 0.12 | 0.096 | 1 |
| Comp. I | 0.12 | 0.120 | 1 |
| 12 | 0.10 | 0.020 | 5 |
| 13 | 0.12 | 0.017 | 4 |

Discussion of results: Even at the relatively high levels used the surfactants of Comparative Examples D–I were not able to produce anti-fog coatings.

Examples 14–18

The anti-fog/anti-reflective compositions of Examples 14a through 14c, 15a through 15c, 16a through 16c, 17a through 17c; and 18a through 18c were made by adding the surfactants given in Table 1 at the concentration indicated in Table 4 to 50 g of a dispersion containing 1.5 weight percent silica prepared by dilution of "Remasol SP-30 Sodium Stabilized Silica Sol" in deionized water. The compositions were coated on both sides of a flame treated 20×30 cm×0.18 mm (7 mil) thick PET film using a number 6 Meyer bar as follows. The first side was coated and immediately dried at 100° C. for 1–2 minutes. Next the second side was coated and dried at 100° C. for 1 to 2 minutes. The coated films were evaluated for fog approximately 2 days after coating using the test described for 12 day fog in Examples 1–11. The results are reported in Table 4.

TABLE 4

| Example Number | Surfactant Concentration (Weight %) | Fog |
| --- | --- | --- |
| 14 a | 0.0080 | 4 |
| 14 b | 0.0120 | 4 |
| 14 c | 0.0200 | 5 |
| 15 a | 0.0080 | 5 |
| 15 b | 0.0120 | 5 |
| 15 c | 0.0200 | 5 |
| 16 a | 0.0080 | 4 |
| 16 b | 0.0140 | 4 |
| 16 c | 0.0200 | 4 |
| 17 a | 0.0500 | 4 |
| 17 b | 0.0130 | 4 |
| 17 c | 0.0063 | 4 |
| 18 a | 0.0080 | 5 |
| 18 b | 0.0040 | 5 |
| 18 c | 0.0020 | 4 |

Discussion of results: The coatings of Examples 14(a–c) and 18(a–c) were spotty. The coated films of Examples 15 and 16 had anti-fog properties and were anti-reflective. The coating compositions of Examples 14a–c, 15a–c, 16a–c and 18a–c provided an anti-reflective surface, as determined using the visual comparison for anti-reflection described in Examples 1–11. The results of visual inspection of the anti-reflective property of the film of Example 17a were poor, but those of 17b and 17c were good, presumably due to the lower level of surfactant.

Examples 19–25

The anti-fog/anti-reflective compositions of Examples 19 through 25 were made by adding the surfactants given in Table 1 at a concentration of 0.015 weight percent to a dispersion containing 2.5 weight percent silica prepared by dilution of "Remasol SP-30 Sodium Stabilized Silica Sol" and 0.25 weight percent of the coupling agent, GPS, commercially available as "A-187" from Union Carbide Chemical & Plastics Company. The compositions were coated on both sides of a flame treated 20×30 cm×0.18 mm (7 mil) thick PET film as described for Examples 14–18. An initial determination of the tendency of the film to fog was made as described below. The remaining samples were hung in a recirculated oven held at 49° C. Film samples were removed at 6, 10, 16, 20 and 26 day intervals and evaluated for the tendency to fog using the following fog test. A new sample was tested at each time period.

Fog Test: Individual film samples were held over a steam source for approximately 5 seconds. The "steam" (i.e., saturated water vapor) source was a container of boiling deionized water which was equipped with an inverted funnel that allowed the steam to exit approximately 10–13 cm above the liquid level through an opening which is approximately 1.3 cm in diameter. The "steam" temperature was approximately 55° C. The film sample was held approximately 5–8 cm above the steam exit. The results were determined subjectively as "good" (the film did not fog), "trace" (a slight amount of fog was detected), and "poor" (the film fogged) on the relative ability to see through the film during the test. The results are reported in Table 5.

TABLE 5

| Ex. No. | Initial | Day 6 | Day 10 | Day 16 | Day 20 | Day 26 |
|---------|---------|-------|--------|--------|--------|--------|
| 19 | good | good | —[1] | good | —[1] | good |
| 20 | good | good | —[1] | good | —[1] | good |
| 21 | good | good | —[1] | good | —[1] | good |
| 22 | good | good | —[1] | trace | —[1] | —[1] |
| 23 | good | —[1] | good | —[1] | good | —[1] |
| 24 | good | —[1] | good | —[1] | good | —[1] |
| 25 | good | —[1] | good | —[1] | good | —[1] |

[1]"—" indicates sample was not tested at this time interval.

Discussion of results: The coated films had good anti-fog properties initially and after at least 20 days of aging, except for the coated film of Example 22 which had a trace of fog after 16 days of aging. All of the coating compositions provided an anti-reflective surface, as determined using the test for anti-reflection described in Examples 1–11.

Example 26

The anti-fog/anti-reflective compositions of Examples 26a through 26d were prepared using the surfactant of Example 9 in a 1.25 weight percent dispersion of "Nalco 1042 Colloidal Silica as $SiO_2$" (14.5 weight percent, particle size 20 nanometers, pH of 2.8), commercially available from Nalco Chemical Company, Naperville, Ill., and 0.125 weight percent of the silane coupling agent, GPS, commercially available as "A-187" from Union Carbide Chemical & Plastics Company. The surfactant was added to 50 g aliquots of the sol at the concentrations indicated in Table 6. The anti-fog/anti-reflective compositions were allowed to sit for 4 hours to allow the silane to hydrolyze. It was observed that this resting time resulted in improved coating quality. The compositions were coated on both sides of a 20×30 cm×0.18 mm (7 mil) thick PET film as described for Examples 14–18. The coated films were dried in an oven at 100° C. for approximately 1–2 minutes. The anti-fog property of the coated films was evaluated using the Fog Test described in Examples 19–25. The anti-reflective property of the film was determined by holding the sample up to the light and against a textured beige colored surface and evaluating its relative light transmission as "good," meaning a significant improvement over uncoated film; "fair," meaning a slight improvement over uncoated film; and "poor," meaning about the same as uncoated film. The results are reported in Table 6.

TABLE 6

| Example Number | Surfactant Concentration (weight %) | Anti-fog | Anti-reflection |
|---------|---------|-----------|-----------|
| 26 a | 0.03 | excellent | good |
| 26 b | 0.05 | excellent | fair |
| 26 c | 0.07 | excellent | poor |
| 26 d | 0.09 | excellent | poor |

Discussion of results: The coated films had excellent anti-fog properties, but the higher the level of surfactant, the better the resistance to fogging. However as the concentration of the surfactant was increased, the anti-reflective property became poorer, indicating an optimal concentration of about 0.03 weight percent for this surfactant.

Examples 27–32

The anti-fog/anti-reflective compositions of Examples 27a through 27c, 28a through 28c, 29a through 29c, 30a through 30c and 31a through 31c were prepared by adding the surfactants given in Table 1 in the amounts given in Table 7 to 50 g of a 1.75 weight percent dispersion of "Remasol SP-30 Sodium Stabilized Silica Sol" in deionized water. The compositions were coated on both sides of a corona discharge treated 20×30 cm×0.18 mm (7 mil) thick PET film as described for Examples 14–18. The initial fog was evaluated using the Fog Test described in Examples 19–25 except that the following rating scale was used: "0" means no fog, "1" means minimal slight haze, "2" means medium fog, and "3" means heavy fog or the same as an uncoated polyester film. The coating quality was determined visually and the following rating scale was used: "very good" means virtually no coating defects, a uniform finish; "good" means only minor coating inconsistencies; "okay" means some coating inconsistencies; "spots" means visible non-wet spots were observed (indicating a need to vary the surfactant concentration or add a wetting agent); and "non-wets" means many coating inconsistencies (indicating the need for a higher concentration of surfactant or the addition of a wetting agent to the coating composition). The results are reported in Table 7. Anti-reflection of the coated films was measured qualitatively by visual observation as described in Example 26. The results are also reported in Table 7.

TABLE 7

| Ex. No. | Amount of 2% surfactant solution added (g) | Surfactant Concentration (weight %) | Coating Quality | Anti-reflection | Initial Fog |
|------|------|-------|----------|------|---|
| 27 a | 0.20 | 0.008 | okay | fair | 0 |
| 27 b | 0.35 | 0.014 | spots | fair | 0 |
| 27 c | 0.50 | 0.020 | spots | fair | 0 |
| 28 a | 0.20 | 0.008 | non-wets | fair | 0 |
| 28 b | 0.35 | 0.014 | non-wets | fair | 0 |
| 28 c | 0.50 | 0.020 | good | good | 0 |
| 29 a | 0.20 | 0.008 | spotty | fair | 0 |
| 29 b | 0.35 | 0.014 | okay | good | 0 |
| 29 c | 0.50 | 0.020 | good | good | 0 |
| 30 a | 0.20 | 0.008 | good | good | 0 |

TABLE 7-continued

| Ex. No. | Amount of 2% surfactant solution added (g) | Surfactant Concentration (weight %) | Coating Quality | Anti-reflection | Initial Fog |
|---|---|---|---|---|---|
| 30 b | 0.35 | 0.014 | good | good | 0 |
| 30 c | 0.50 | 0.020 | good | good | 0 |
| 31 a | 0.20 | 0.008 | good | good | 0 |
| 31 b | 0.35 | 0.014 | good | good | 0 |
| 31 c | 0.50 | 0.020 | very good | good | 0 |
| 32 a | 0.20 | 0.008 | good | good | 0 |
| 32 b | 0.35 | 0.014 | good | fair | 0 |
| 32 c | 0.50 | 0.020 | good | fair | 0 |

Discussion of Results:

The results indicate that within this set of surfactants better wetting is achieved at higher levels of surfactant. Example 27(a)–(c) showed an improvement and Examples 28(a)–(c), 29(a)–(c), 30(a)–(c), 31(a)–(c), and 32(a)–(c) showed a significant improvement in the anti-reflective property. All samples had good initial anti-fog properties.

Examples 33–41 and Comparative Examples J–L

The anti-fog/anti-reflective compositions of Examples 33 through 42 and the anti-reflective compositions of Comparative Examples J through L were prepared as follows. A master batch of colloidal silica was made from "Remasol SP-30 Sodium Stabilized Silica Sol (30 percent solution)," GPS, commercially available as "G6720" from Huls, Piscataway, N.J., and deionized water in the following amounts:

| Material | Amount (g) |
|---|---|
| Deionized Water | 142,600 |
| Colloidal silica | 8,840 |
| GPS | 265 |

The materials were added in the order listed with a minimum of 5 minutes of mixing between additions. The mixture was allowed to stir overnight. The surfactant listed in Table 1 in the amount and concentration (in deionized water) described in Table 8 was added to 18,900 gram aliquots of the master batch solution. The compositions were coated onto a 30.9 cm wide, 0.18 cm (7 mil) thick corona discharge treated PET film using a roll coater and air knife as described in Examples 1–11. The air knife was operated at a pressure of approximately 5–13 cm of water. The setting varied with each composition in order to attain the desired thickness of coating which after drying had a violet to slightly blue hue. The coated films were immediately passed into a forced air oven at a temperature of 77° C. The dwell time in the oven was less than 2 minutes. The second side was coated in a similar manner. All of the coating compositions provided an anti-reflective surface, as determined using the test for anti-reflection described in Example 26. The coating quality was evaluated visually and the following rating scale was used: "excellent" means virtually no coating defects, a uniform finish; "very good" and "good" indicate only minor coating inconsistencies; "okay" means some coating inconsistencies; and "poor" means many coating inconsistencies. The results are reported qualitatively in Table 8.

TABLE 8

| Ex. No. | Amount of surfactant solution added (g of percent by wt. solution) | Surfactant Concentration (weight %) | Coating Quality |
|---|---|---|---|
| 33 | 56.8 (10%) | 0.030 | excellent |
| 34 | 113.4 (5%) | 0.030 | excellent |
| 35 | 66.5 (4%) | 0.014 | very good |
| 36 | 94.6 (4%) | 0.020 | good |
| 37 | 71.0 (4%) | 0.015 | good |
| 38 | 94.6 (4%) | 0.020 | very good |
| 39 | 94.8 (4%) | 0.020 | okay |
| 40 | 71.0 (4%) | 0.015 | excellent |
| 41 | 142.0 (2%) | 0.015 | very good |
| Comp. J | 37.8 (4%) | 0.008 | good |
| Comp. K | 56.7 (4%) | 0.012 | good |
| Comp. L | 66.2 (4%) | 0.014 | good |

The coated films were aged using an Aging Test described below.

Aging Test: Multiple coated film samples were cut, 5 cm×15 cm. Great care was taken to keep the coated film samples from becoming contaminated. Personnel wore cotton gloves and samples were not placed in packaging materials which could result in surface contamination. A magazine was made from polystyrene foam core/paper board, with razor slits approximately 1.3 cm deep and 1.3 cm apart cut into one edge of the board. The coated film samples were placed in the magazine so that adjacent samples were not touching and so that substantially the entire surface area of the sample was exposed to the environment. The sample loaded magazines were placed in an oven capable of totally recirculating and recycling air. The oven conditions were: 1) a recirculation rate of 1.67 volumes/minute, 2) a temperature of 30° C., and 3) a relative humidity of 60 percent. It was possible that in some samples an increase in fogging was a result of surface contamination due to the air quality inside the oven. Therefore, relative differences may be more important than the actual values. Film samples were removed at regular time intervals of 7, 14, 28, 56 and 84 days and evaluated by the Wetting Test described below. The "initial" sample was evaluated after standing at room temperature for 24 to 48 hours after coating.

Wetting Test: Each film sample was conditioned at 23° C. and 50 percent relative humidity for a minimum of 8 hours before and during testing. Care was taken to ensure that the film samples were not contaminated and that exposure to the environment did not result in decreased wetting. The film samples were placed on a clean flat horizontal surface with the side to be tested up. A 3 microliter drop of deionized and distilled water containing 0.07% by weight "Wool Fast Brilliant Red R.L. Dye," commercially available from Pylam, Garden City, N.Y., from an accurate syringe was gently placed on the surface by holding the syringe vertically and just touching the drop to the surface so that the drop did not fall and impact the surface. The drop was allowed to spread to its maximum extent and completely dry. The diameter of the drop was determined by placing the film over a paper with premeasured circles of varying diameters. The average drop diameter was recorded. The dye did not interact with the surfactant system being tested, as verified by comparing the results with results without the dye. The results of the Wetting Test are reported in Table 9.

TABLE 9

Wetting Value after Aging

| Ex. No. | Initial (mm) | Day 7 (mm) | Day 14 (mm) | Day 28 (mm) | Day 56 (mm) | Day 84 (mm) |
|---|---|---|---|---|---|---|
| 33 | 9.0 | —[1] | 8.1 | —[1] | 4.3 | 3.9 |
| 34 | 8.6 | 9.1 | 6.6 | 5.0 | 4.6 | 3.8 |
| 35 | 8.8 | 8.5 | 5.5 | 4.4 | 4.0 | 3.9 |
| 36 | 8.0 | 7.5 | 6.7 | 4.7 | 4.3 | 4.0 |
| 37 | 8.3 | 8.5 | 6.0 | 6.1 | 4.2 | — |
| 38 | 8.6 | 7.4 | 5.4 | 4.9 | 4.0 | 3.8 |
| 39 | 9.2 | 7.0 | 5.8 | 4.4 | 4.4 | 3.8 |
| 40 | 8.7 | 7.0 | 5.8 | 4.4 | 4.4 | 3.8 |
| 41 | 7.9 | 6.8 | 5.4 | 4.6 | 4.0 | 3.8 |
| Comp. J | 8.7 | 4.3 | 3.9 | 3.8 | 3.8 | 3.6 |
| Comp. K | 8.6 | 5.6 | 4.4 | 4.0 | 3.8 | 3.6 |
| Comp. L | 8.9 | 5.1 | 4.6 | 3.9 | 3.9 | 3.6 |

[1]"—" means sample was not tested at that time interval.

Discussion of results: Uncoated PET film had a wetting value of 2.75 mm for comparison. Actual breathing tests such as those described in Examples 1–11 indicated that once the wetting values fall below about 4.1 mm the fogging was unacceptable for use in a surgical mask application. The surfactants of the present invention produced coated films with acceptable wetting values (indicating a resistance to fogging) beyond day 28 and several beyond day 56 in this accelerated aging test. The coated films of Comparative Examples K–L lost their anti-fog properties between day 14 and day 28 and the coated film of Comparative Example J by day 14.

Aging in Sealed Environments

In order to better understand the aging properties of the various surfactants and whether environmental contamination of the films decreases their anti-fog property, coated films from Examples 33–35, 38, 40–41, and Comparative Example J were conditioned in a 25° C./50% relative humidity environment overnight (approximately 12 hours) and were placed in two sets of sealed jars. Separate jars were used for coated films containing different surfactants. Jars in Set 1 (Dry) contained only the coated films, while jars in Set 2 (Wet) contained the coated films and a small vial of deionized water sufficient to ensure it did not completely evaporate. The water in the vial did not contact the films directly, but served as a source of high humidity. The jars were placed in a 40° C. oven and films were periodically withdrawn and tested for Wetting as described above. The results are reported in Table 10 for dry aging and Table 11 for wet aging. The coated films containing the surfactants of the present invention performed extremely well as durable anti-fogging agents when maintained in a sealed chamber. The fogging characteristics did not significantly decrease even after 56 days. The wetting of Comparative Example J fell rapidly even in a sealed container. While not being bound to any theory, the results indicated that loss of anti-fog properties may be due to environmental surface contamination of the coated films. Loss of anti-fog properties in the comparative example appeared to be due to other causes since the anti-fog property decreased very rapidly even in a sealed container.

TABLE 10

Set 1 "Dry" Wetting Value after Aging

| Ex. No. | Initial (mm) | Day 7 (mm) | Day 14 (mm) | Day 28 (mm) | Day 56 (mm) | Day 84 (mm) |
|---|---|---|---|---|---|---|
| 33 | 8.7 | 8.2 | 7.4 | 9.0 | 9.6 | 8.7 |
| 34 | 8.0 | 7.2 | 7.4 | 8.9 | 8.2 | 9.3 |
| 35 | 8.8 | 7.6 | 7.2 | 9.1 | 9.5 | 7.8 |
| 38 | 8.6 | 6.3 | 6.9 | 8.1 | 8.9 | 8.5 |
| 40 | 8.7 | 7.4 | 7.7 | 8.6 | 9.1 | 8.2 |
| 41 | 7.9 | 6.6 | 6.3 | 8.9 | 8.8 | 8.2 |
| Comp. J | 8.7 | 4.7 | 4.5 | 4.8 | 3.8 | 4.0 |

TABLE 11

Set 2 "Wet" Wetting Value after Aging

| Example Number | Initial (mm) | Day 7 (mm) | Day 14 (mm) | Day 28 (mm) | Day 56 (mm) |
|---|---|---|---|---|---|
| 33 | 8.7 | 8.1 | 8.3 | 8.5 | 7.5 |
| 34 | 8.0 | 8.2 | 7.6 | 8.0 | 7.8 |
| 35 | 8.8 | 7.2 | 7.4 | 8.4 | 6.9 |
| 38 | 8.6 | 7.1 | 6.6 | 6.7 | 6.7 |
| 40 | 8.7 | 8.4 | 8.2 | 7.7 | 7.8 |
| 41 | 7.9 | 7.6 | 7.3 | 8.1 | 7.3 |
| Comp. J | 8.7 | 4.4 | 4.1 | 3.9 | 4.1 |

Comparative Examples M–N
Preparation of Surfactant

Lithium stearate was prepared by: a) dissolving 2.2 grams of lithium hydroxide monohydrate commercially available from Fisher Scientific, Pittsburgh, Pa., in approximately 60 mL of water and heating to about 80° C. until the lithium hydroxide was completely dissolved; b) heating 142 grams of stearic acid commercially available from Fisher Scientific, to about 80° C. to melt the stearic acid and then adding about 10 mL of isopropyl alcohol commercially available from Fisher Scientific, while stirring; and c) adding part a) to part b) while still hot, stirring to form a loose dispersion, continuing to stir for 10–15 minutes while allowing the dispersion to cool. The resulting mass was washed twice by adding about 20 ml of warm water and filtering through a paper filter and repeating the sequence. The washed residue was pressed in the filter to squeeze out the excess wash water and was air-dried at about 45° C. until it reached a constant weight. A loose fine powder was obtained.

Preparation of Anti-reflective Coated Films

A 2 weight percent solution of surfactant was prepared by dissolving 1 gram of surfactant in 49 grams of deionized water. A master batch of silica sol with a silica solids concentration of 1.75 weight percent was prepared by adding 46.67 grams of "Remasol SP-30 Sodium Stabilized Silica Sol" (30 percent solution) to 753.3 grams deionized water. The anti-reflective composition of comparative Example M was prepared by mixing the surfactant concentrate into 50 grams of the dilute silica dispersion. The anti-reflective composition of Comparative Example N was prepared similarly, except that the surfactant described in Table 1 was used in place of lithium stearate in the amount and concentration given in Table 12. The compositions were coated as described in Examples 14–18. The coated films were aged in an oven as described in Examples 33–42 and evaluated using the Wetting Test also described in Examples 33–42. Three coated films from Example 34 were reevaluated for comparison. The results are reported in Table 13.

TABLE 12

| Example Number | Amount of 2% surfactant solution added (g) | Surfactant Concentration (weight %) |
|---|---|---|
| Comp. M | 0.35 | 0.014 |
| Comp. N | 0.50 | 0.020 |

TABLE 13

| | Wetting Value after Aging | | | | |
|---|---|---|---|---|---|
| Ex. No. | Initial (mm) | Day 7 (mm) | Day 14 (mm) | Day 28 (mm) | Day 35 (mm) |
| Comp. M | 8.64 | 3.84 | 3.66 | 3.29 | 3.29 |
| Comp. N | 8.46 | 4.01 | 3.56 | 3.29 | 3.29 |
| 34 | 8.55 | — | 6.37 | — | 4.20 |

[1]"—" indicates sample was not evaluated at this time interval.

Discussion of results: The results clearly illustrated that the stearate salt surfactants did not provide a durable anti-fog coating. These results were in contrast to the carboxylate of Example 5 and illustrated the importance of including an additional polar substituent when the surfactant is a carboxylate.

Example 42

An anti-fog/anti-reflective coating composition was prepared containing:

| Component | Amount in weight % |
|---|---|
| Deionized water | 97.98 |
| "Remasol SP-30 Sodium Stabilized Silica Sol (30 percent solution)" from Remet Corporation | 1.83 (as silica) |
| GPS commercially available as "A-187" from Union Carbide Chemical & Plastics Company | 0.18 |
| "Fluorad ™ FC-95 Fluorochemical Surfactant" from 3M Company | 0.015 |

The composition was stirred overnight and coated onto a flame treated 0.1 mm polyethylene terephthalate (PET) film according to the method described in Examples 1–11. The coating quality was evaluated as described in Examples 33–41 and found to be "excellent." The coated film was also evaluated for anti-fogging using the Wetting Test described in Examples 33–41. Both sides of the coated film had a 7.2 mm average drop diameter when evaluated at the "initial" time interval. The coated film and an uncoated PET film were evaluated for anti-reflective properties using a "Perkin-Elmer Spectraphotometer Model 552A" commercially available from Coleman Instrument Division, Oakbrook, Ill. The percent transmission of the coated and uncoated film are reported in Table 14.

TABLE 14

| | Percent Transmission | | | | |
|---|---|---|---|---|---|
| | Wave Length of Incident Light | | | | |
| Example Number | 500 nm (%) | 550 nm (%) | 600 nm (%) | 650 nm (%) | 700 nm (%) |
| 42 | 95.8 | 97.0 | 97.6 | 98.2 | 98.0 |
| Uncoated film | 84.0 | 86.0 | 86.0 | 86.0 | 86.0 |

The results indicated that the coated film of Example 42 had both exceptional anti-fog properties, as shown by the large average drop diameter, and anti-reflective properties, as shown by the 11–12.2 percent increase in light transmission over the uncoated film.

Examples 43 to 49 and Comparative Examples O to T

The anti-fog/anti-reflective coating compositions of Examples 43–49 and the anti-reflective coating compositions of Comparative Examples O–T were prepared using a stock solution comprising 3,437 grams (g) of deionized water, 2.0 g of concentrated ammonium hydroxide, 326 g of "Nalco 2326 Colloidal Silica" (Nalco Chemical Co.), and 4.24 g of 3-aminopropyl-triethoxysilane (APS) coupling agent. 0.1 g amounts of the various surfactants described in Table 1 were added to 200 g portions of the stock solution to prepare each coating composition. To the coating compositions of Examples 45, 46, and 48, and Comparative Examples R, S and T, 0.6 g of a 10% aqueous solution of "Triton X-100," a wetting agent commercially available from Union Carbide Chemical & Plastics Co., was also added as indicated in Table 15, hereinbelow.

Each coating composition was applied to both sides of a polyvinylidene chloride primed 0.1 mm thick polyethylene terephthalate film using a number 6 wire-wound rod (Meyer bar) to provide a coating about 1,000 Å thick on each side. The coated films were dried at 100° C. for about 1 minute on each side and allowed to cool to room temperature. Each coated film was then evaluated for its anti-fogging properties using the following test procedure: A test apparatus comprising a laboratory stirring hot plate with a variable temperature control, a 1,000 milliliter (ml) glass beaker containing 500 ml of water, a 10 cm (4 inch) diameter polypropylene funnel placed in an inverted position on the flared rim of the beaker, and a 10 cm (4 inch) polypropylene tube secured to the distal end of the funnel discharge spout was constructed. The water was heated to boiling with stirring thereby generating a "steam" jet from the tube secured to the funnel. The "steam" temperature approximately 7.6 cm (3 inches) above the distal end of the tube was about 55° C. Coated films measuring 25.4 cm×30.5 cm (10 in.×12 in.) were passed through the "steam" jet approximately 7.6 cm (3 inch) above the tube outlet with a total exposure time of about 1 second. The coated substrates were then observed to determine whether a fog of condensed water vapor droplets had formed, significantly reducing the transparency of the substrate such that it could not be readily seen through. The results are reported in Table 15 along with the time required for samples that were not completely fogged to dry. The "transmittance" (i.e., the percentage point increase in the transmission of the coated substrate as compared to an uncoated substrate) was measured using ASTM Test Method D 1003-61, Procedure A (as reapproved in 1988), incorporated herein by reference. The results are also reported in Table 15.

TABLE 15

| Example Number | Wetting Agent | Fog Formation | Drying Time (Seconds) | Transmittance (Percentage Point Increase) |
|---|---|---|---|---|
| 43 | No | No | 14 | NM |
| 44 | No | No | 30 | NM |
| 45 | Yes | No | 24 | 6.0 |
| 46 | Yes | No | 20 | 3.9 |
| 47 | No | Partial | 14 | 7.1 |
| 48 | Yes | No | 8 | NM |
| 49 | No | No | 11 | NM |
| Comp. O | No | Yes | NT | NM |
| Comp. P | No | Yes | NT | NM |
| Comp. Q | No | Yes | NT | NM |
| Comp. R | Yes | Yes | NT | NM |
| Comp. S | Yes | Yes | NT | NM |
| Comp. T | Yes | Yes | NT | NM |

NT = Not tested because substrate completely fogged.
NM = Not measured.

The data in Table 15 illustrates the benefit of a coating composition that comprises an inorganic metal oxide (silica) and a surfactant of the present invention (i.e., either a potassium salt of a perfluoroaliphatic sulfonamido carboxylate compound or a lithium salt of an anionic perfluoroaliphatic radical-containing compound) in providing anti-reflection and anti-fogging properties to a film coated therewith. Coating compositions utilizing the nonionic fluorochemical compounds of Comparative Examples O, P, Q, R, S and T did not exhibit anti-fogging properties.

Examples 50–52

Comparative Examples U–Y

The anti-fog/anti-reflective coating compositions for use in Examples 50–52 and the anti-reflective coating compositions for use in Comparative Examples U–Y were prepared as described in Examples 43–49. The surfactant used in each composition was "Fluorad™ FC-95 Fluorochemical Surfactant" from 3M Company. Use of the wetting agent, "Triton X-100", is indicated in Table 16. Each composition was applied to both a polyvinylidene chloride (PVDC) primed 0.1 mm thick polyethylene terephthalate (PET) film (Examples 50 and 52 and Comparative Examples U and W) and an unprimed 0.1 mm thick PET film (Example 51 and Comparative Examples V, X and Y) using the method described for Examples 43–49 and using either a number 6 (Comparative Examples U, V, W and X) or a number 7 (Examples 50–52 and Comparative Example Y) wire wound rod (Meyer bar), as indicated in Table 16. The coated films were dried and the fogging evaluated as described in Examples 43–49. The results are reported in Table 16.

TABLE 16

| Example Number | Primed Film | Wetting Agent | Meyer Bar Number | Fog |
|---|---|---|---|---|
| Comp. U | yes | no | 6 | yes |
| 50 | yes | no | 7 | no |
| Comp. V | no | no | 6 | yes |
| 51 | no | no | 7 | no |
| Comp. W | yes | yes | 6 | yes |
| 52 | yes | yes | 7 | no |
| Comp. X | no | yes | 6 | yes |
| Comp. Y | no | yes | 7 | yes |

Comparative Examples U–X illustrate that films coated with a number 6 Meyer bar fogged. The coatings reproduced in Comparative Examples U–X appeared thin since the coatings had a gold hue. Therefore, in Examples 50–52 a number 7 Meyer bar was used to give a thicker coating. The coated films made using the number 7 Meyer bar were good anti-fog films. The results in Table 16 show that on either PVDC primed PET or unprimed PET as the coating thickness became thinner the film exhibited fogging. The reason for this was not clear. In addition, the presence of the wetting agent seemed to cause the fogging of the coated films to increase as can be seen by comparing the fogging results of Comparative Example Y to Example 51.

Comparative Examples U and V and examples 50 and 51 were replicated (again using a number 6 Meyer bar) except the "Fluorad™ FC-95 Fluorochemical Surfactant" concentrations were adjusted from 0.05 weight percent to 0.04 weight percent and 0.02 weight percent. The fogging results were exactly the same as the results shown in Table 16 for Comparative Examples U and V and Examples 50 and 51 demonstrating that decreasing the amount of surfactant did not improve fogging.

Examples 53–60

Comparative Examples Z–AC

Coating compositions were prepared as described for Examples 43–49. In one batch the silane coupling agent, aminopropyltriethoxysilane (APS), was omitted (Examples 53–56). In another batch the silane coupling agent, APS, was replaced with glycidoxypropyl-trimethoxysilane (GPS), commercially available as "A-187" from Union Carbide Chemical & Plastics Company (Examples 57–60). The surfactant used in all compositions was "Fluorad™ FC-120 Fluorochemical Surfactant" from 3M Company. Batches of the above-described compositions were made with and without the wetting agent, "Triton™ X-100" from Union Carbide Chemical & Plastics Co. Each coating composition was applied to both sides of an unprimed 0.1 mm thick PET film using either a number 6 (Examples 53, 55, 57 and 59, and Comparative Examples Z and AB) or a number 7 wire wound rod Meyer bar (Examples 54, 56, 58 and 6, and Comparative Examples AA and AC). The coatings were dried and the fogging evaluated as described for Examples 43–49. The results of the fog test are given in Table 17.

TABLE 17

| Example Number | Silane Coupling Agent Type | Wetting Agent | Meyer Bar Number | Fog |
|---|---|---|---|---|
| Comp. Z | APS | no | 6 | yes |
| Comp. AA | APS | no | 7 | yes |
| Comp. AB | APS | yes | 6 | yes |
| Comp. AC | APS | yes | 7 | yes |
| 53 | none | no | 6 | no |
| 54 | none | no | 7 | no |
| 55 | none | yes | 6 | no |
| 56 | none | yes | 7 | no |
| 57 | GPS | no | 6 | no |
| 58 | GPS | no | 7 | no |
| 59 | GPS | yes | 6 | no |
| 60 | GPS | yes | 7 | no |

The films coated with a composition containing APS as the silane coupling agent (Comparative Examples Z, AA, AB and AC) fogged both with and without the addition of the wetting agent. The coated films which were applied using a number 6 Meyer bar (Comparative Examples Z and AB) appeared thin since the coatings had a gold hue, so a number 7 Meyer bar (Comparative Examples AA and AC) was used to get a thicker coating having a violet or blue hue. Regardless of the coating thickness, the coated films containing APS fogged. Unlike the coated films containing "Fluorad™ FC-95 Fluorochemical Surfactant" in Examples 50–52, coating thickness did not effect the anti-fog property. "Fluorad™ FC-120 Fluorochemical Surfactant" is an ammonium salt of a perfluoroaliphatic sulfonate. While not being bound to theory, in the presence of an organic amine base, such as APS, an ionic exchange could occur especially on heating which would drive off ammonia and form the APS salt of the perfluorinated sulfonate. The APS salt did not appear to be an effective anti-fog agent. In the absense of (APS) or with the coupling agent GPS, "Fluorad™ FC-120 Fluorochemical Surfactant" was a very effective anti-fog agent with or without the addition of wetting agent (see Examples 53–60). "Triton™ X-100" did not help prevent fogging and was not an effective anti-fog surfactant as shown in Comparative Example A after 12 days.

Examples 61–63

Comparative Examples AD–AH

Coating composition was prepared as described in Examples 43–49. Identical coating compositions were also prepared, except that the silane coupling agent, APS, was omitted (Examples 61–63 and Comparative Example AH). The surfactants used in the compositions are described in Table 18. The wetting agent if used was "Triton™ X-100." The coating compositions were applied to both sides of an unprimed flamed treated 0.1 mm thick PET film using a number 7 wire wound rod Meyer bar. The coatings were dried and the fogging evaluated as described in Examples 43–49. The results of the fog test are given in Table 18.

TABLE 18

| Example Number | Surfactant | Silane Coupling Agent | Wetting Agent | Fog |
|---|---|---|---|---|
| Comp. AD | $C_4F_9SO_3H$ | APS | no | yes |
| Comp. AE | FC-93 | APS | no | yes |
| Comp. AF | $C_4F_9SO_3H$ | APS | yes | yes |
| Comp. AG | FC-93 | APS | yes | yes |
| 61 | $C_4F_9SO_3H$ | none | no | no |
| 62 | FC-93 | none | no | no |
| Comp. AH | $C_4F_9SO_3H$ | none | yes | yes |
| 63 | FC-93 | none | yes | no |

The films coated with a composition containing either surfactant, $C_4F_9SO_3H$ or "Fluorad™ FC-93 Fluorochemical Surfactant," and APS as the silane coupling agent fogged both with and without the addition of the wetting agent (Comparative Examples AD, AE, AF and AG). FC-93 is an ammonium salt of a perfluoroaliphatic sulfonate. $C_4F_9SO_3H$ is a very strong acid. These results were consistent with those for the "Fluorad™ FC-120 Fluorochemical Surfactant" from 3M Company in Examples 53–60 and Comparative Examples Z–AC and seem to indicate that in the presence of an organic base, such as APS, an ionic exchange occurs forming the APS salt of the perfluorinated sulfonate. The salt did not appear to be an effective anti-fog agent. However, in the absence of an additional amine (APS) both $C_4F_9SO_3H$ or the "Fluorad™ FC-93 Fluorochemical Surfactant" from 3M Company were very effective anti-fog agents.

The coatings containing surfactant, $C_4F_9SO_3H$ or "Fluorad™ FC-93 Fluorochemical Surfactant," without the silane coupling agent or the wetting agent (Examples 61 and 62) did not fog. Addition of the wetting agent to the coating composition containing $C_4F_9SO_3H$ (Comparative Example AH) caused the film to fog while addition of the same wetting agent to the coating composition containing "Fluorad™ FC-93 Fluorochemical Surfactant" did not result in fogging.

We claim:

1. A coating composition which imparts anti-reflection and anti-fogging properties to a substrate having at least one surface coated therewith, the coating composition comprising:

(a) an inorganic metal oxide sol capable of forming a porous inorganic metal oxide network which provides anti-reflective properties to a substrate; and (b) a surfactant having a solubility in water of less than about 10 percent by weight at 23° C. and comprised of at least one hydrophobic group and at least one hydrophilic anionic group, wherein:

(i) the hydrophilic anionic group comprises an anion selected from the group consisting of $—OSO_2O^-$, $—SO_2O^-$, $—CO_2^-$, $(—O)_2P(O)O^-$, $—OP(O)(O^-)_2$, $—P(O)(O^-)_2$, $—P(O^-)_2$, $—OP(O^-)_2$, $(—SO_2)_2N^-$, $—SO_2N(R)^-$, $(—SO_2)_2C^-H$, and $—N^+(R)_2(CH_2)_xL'$, wherein R is hydrogen, an alkyl group which is unsubstituted or substituted with atoms independently selected from the group consisting of oxygen, nitrogen and sulfur, or an alkylene carboxyl group, which alkyl or alkylene carboxyl group comprises about 1 to 10 carbon atoms; x is 1 to 4; and L' is selected from the group consisting of $—OSO_2O^-$, $—SO_2O^-$, $(—O)_2P(O)O^-$, $—OP(O)(O^-)_2$, $—P(O)(O^-)_2$ and $—CO^-_2$; and wherein each anionic group is associated with or covalently bound to at least one cation, which cation is selected from the group consisting of $H^+$, $Na^+$, $K^+$, $Li^+$, $Ca^{+2}$, $Mg^{+2}$, $Sr^{+2}$, $Al^{+3}$, and $R''A^+$, wherein R" is R or R' wherein R is hydrogen or an alkyl or cycloalkyl group of about 1 to 10 carbon atoms, and R' is covalently bonded to the surfactant molecule and is an alkyl bridging group of 1 to 10 carbon atoms, and $A^+$ is $N^+R_3$, a guanidinium ion optionally substituted with oxygen, nitrogen or sulfur atoms, or $N^+B$ wherein B comprises 3 to 7 atoms selected from the group consisting of carbon, nitrogen, sulfur and oxygen atoms which complete the nitrogen containing heterocyclic ring; and wherein any R or R' group may be unsubstituted or substituted with atoms independently selected from the group consisting of oxygen, nitrogen or sulfur; the cation selected such that the net charge of the surfactant molecule is neutral; and (ii) wherein the hydrophobic group comprises a hydrocarbon chain comprising at least 4 carbon atoms, or a perfluorinated radical comprising at least 3 carbon atoms; wherein the coating composition when coated on at least one side of a light transmissive substrate and dried provides a coated substrate with:

(1) a porous inorganic metal oxide network of uniform average thickness;

(2) a drop diameter of at least about 4 mm when tested in accordance with the Wetting Test described herein; and (3) a percent transmission at 550 nm which is at least 3 percent greater than that of the uncoated substrate.

2. The coating composition of claim 1 wherein the surfactant has the general formula:

$\{(R)_a L^{-c}\}_d (M^{+b})_e$ wherein:
R is selected from the group consisting of a perfluorinated allkyl or cycloalkyl group of about 3 to 18 carbon atoms; a polyethoxylated perfluoroalkyl or perfluorocycloalkyl substituted alcohol comprising about 3 to 18 perfluorinated carbon atoms and about 0 to 30 non-fluorinated carbon atoms; a perfluoroalkyl substituted alkyl or alkenyl group of about 3 to 18 perfluorinated atoms and about 0 to 30 non-fluorinated carbon atoms, which alkyl or alkenyl group is unsubstituted or comprises oxygen nitrogen or sulfur atoms within or substituted upon the alkyl or alkenyl chain; an alkyl or alkenyl group of about 4 to 36 carbon atoms, which alkyl or alkenyl group is unsubstituted or comprises oxygen, nitrogen or sulfur atoms within or substituted upon the alkyl or alkenyl chain; an aralkyl group of about 7 to 36 carbon atoms, which aralkyl group is unsubstituted or independently substituted in available positions by oxygen, nitrogen or sulfur atoms; and a polyethoxylated or polypropoxylated alkyl or aralkyl group of about 7 to 36 carbon atoms;

L is selected from the group consisting of a sulfate, sulfonate, phosphate, phosphonate, sulfonimide, sulfonamide, carboxylate, phosphonite, phosphite and disulfonylmethide groups, and amphoteric alkyl forms thereof; provided that when L is a carboxylate, the surfactant molecule further comprises an additional polar heteroatom or substituent no further than four atoms removed from the carboxylate group, wherein said polar substituent is selected from the group consisting of ether, amide, alcohol, carboxyl, ester, thioester, urea, and urethane groups, and combinations thereof;

M is selected from the group consisting of hydrogen, sodium, potassium, lithium, ammonium, calcium, magnesium, strontium, aluminum and R"A$^+$, wherein R" is R or R', wherein R is hydrogen or an alkyl or cycloalkyl group of about 1 to 10 carbon atoms and R' is covalently bonded to the surfactant molecule and is an alkyl bridging group of about 1 to 10 carbon atoms which is unsubstituted or substituted in available positions with oxygen, nitrogen or sulfur atoms; and A$^+$ is selected from the group consisting of N$^+$R$_3$; a guanidinium ion optionally substituted with oxygen, nitrogen or sulfur atoms; or a heterocyclic N$^+$B wherein B comprises 3 to 7 atoms selected from the group consisting of carbon, nitrogen, sulfur and oxygen atoms which complete the nitrogen containing heterocyclic ring;

a and c are independently 1 or 2;
b and d are independently 1, 2 or 3, and
e is equal to (c times d)/b, or 0.

3. The coating composition of claim 1 wherein the surfactant is a perfluoroaliphatic anionic salt.

4. The coating composition of claim 2 wherein R is CF$_3$C$_n$F$_{2n}$—, wherein n is about 2 to 17.

5. The coating composition of claim 3 wherein the surfactant is a lithium, sodium or potassium salt of an anionic perfluoro-containing compound.

6. A coating composition according to claim 5 wherein the surfactant comprises a hydrophilic anionic group selected from the group consisting of sulfate, sulfonate, phosphate, phosphonate, sulfonimide, sulfonamide, carboxylate, phosphonite, phosphite and disulfonylmethide groups, and amphoteric forms thereof.

7. The coating composition of claim 1 wherein the surfactant is a perfluoroalkyl-substituted aliphatic anionic salt.

8. The coating composition of claim 2 wherein R is (C$_n$F$_{2n+1}$)$_z$ R$^2$—,
wherein:
n is about 2 to 36;
R$^2$ is a branched or straight chain alkylene or aralkylene group of about 2 to 36 carbon atoms, which is unsubstituted or independently substituted in available positions with oxygen, nitrogen or sulfur atoms, provided that R$^2$ is selected such that R comprises at least 7 carbon atoms; and
z is about 1 to 3.

9. The coating composition of claim 2 wherein:
R is C$_n$H$_{2n+1}$(R$^2$)$_m$—; and wherein
n is about 4 to 36;
R$^2$ is an alkyl or aralkyl group of about 1 to 36 carbon atoms, which is unsubstituted or independently substituted in available positions with oxygen, nitrogen or sulfur atoms;
m is 0 or 1, and
L is SO$_3^-$ or SO$_4^-$.

10. The coating composition of claim 1 wherein the surfactant is a sulfate or sulfonate of a polyethoxylated alkyl or aralkyl alcohol or carboxylic acid wherein the alkyl or aralkyl group comprises from 4 to 36 carbon atoms.

11. The coating composition of claim 2 wherein:
R is C$_n$H$_{2n+1}$(CO)$_p$O(CH$_2$CH$_2$O)$_y$CH$_2$CH$_2$—; and wherein
n is about 4–36;
p is 0 or 1;
y is about 1–100; and
L is SO$_4^-$ or SO$_3^-$.

12. The coating composition of claim 2 wherein:
R is selected from the group consisting of (C$_n$H$_{2n+1}$)$_q$(C$_6$H$_{5-q}$)— and (C$_n$H$_{2n+1}$)$_q$C$_{10}$H$_{7-q}$—; and wherein
n is about 4 to 36;
q is 1 to 3; and
L is SO$_3^-$ or SO$_4^-$.

13. The coating composition of claim 1 wherein the surfactant is selected from the group consisting of alkylbenzene sulfonate, alkylbenzene sulfate, alkylnaphthalene sulfonate and alkylnaphthalene sulfate, wherein the alkyl group comprises from 4 to 36 carbon atoms.

14. The coating composition of claim 1 wherein the surfactant comprises a carboxylate group and at least one other polar substituent selected from the group consisting of ether, amide, ester, alcohol, carboxyl, urea and urethane groups, wherein said other polar substituent is from 1 to 4 atoms removed from the carbon of the carboxylate group.

15. The coating composition of claim 1 wherein the surfactant is an ethoxylated or polyethoxylated alkyl or aralkyl alcohol carboxylate wherein the alkyl or aralkyl group comprises from 4 to 36 carbon atoms.

16. The coating composition of claim 2 wherein:
R is (C$_n$H$_{2n+1}$)$_q$(C$_6$H$_{5-q}$)$_m$O(CH$_2$CH$_2$O)$_y$CH$_2$—,
and wherein:
n is about 4 to 36,
m is 0 or 1,
q is 1 or 2;
y is about 1 to 100; and
L is CO$_2^-$.

17. The coating composition of claim 1 wherein the surfactant is a glycinate, comprising from 4 to 36 carbon atoms.

18. The coating composition of claim 2 wherein:

R is $R^2—C(O)N(R^3)CH_2—$ wherein:

$R^2$ is a branched or straight chain alkyl or aralkyl of about 4 to 36 carbon atoms, which is unsubstituted or independently substituted in available positions with oxygen, nitrogen or sulfur atoms; and $R^3$ is hydrogen or an alkyl group of about 1 to 10 carbon atoms, which is unsubstituted or independently substituted in available positions by oxygen, nitrogen or sulfur atoms; and wherein L is $CO_2—$.

19. The coating composition of claim 1 wherein the surfactant is a dialkyl sulfosuccinate wherein each alkyl group comprises from 4 to 36 carbon atoms.

20. The coating composition of claim 2 wherein:

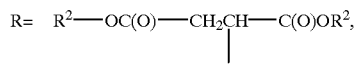

and wherein $R^2$ is a branched or straight chain alkyl group of about 4 to 36 carbon atoms, or an aralkyl group of about 7 to 36 carbon atoms, which alkyl or aralkyl group is unsubstituted or independently substituted in available positions by oxygen, nitrogen and/or sulfur atoms; and L is $SO_3^-$.

21. The coating composition of claim 1 wherein the surfactant is an alkyl or aralkyl isethionate derivative, wherein the alkyl group comprises from 4 to 36 carbon atoms and the aralkyl group comprises from 7 to 36 carbon atoms.

22. The coating composition of claim 2 wherein:

R is $R^2—C(O)OCH_2CH_2—$, and $R^2$ is an alkyl group of about 4 to 36 carbon atoms, or an aralkyl group of about 7 to 36 carbon atoms, which alkyl or aralkyl group is unsubstituted or independently substituted in available positions with oxygen, nitrogen or sulfur atoms; and L is $SO^-_3$.

23. The coating composition of claim 1 wherein the surfactant is an N-acyltaurine derivative comprising about 4 to 36 carbon atoms.

24. The coating composition of claim 2 wherein:

R is $R^2—C(O)N(R^3)CH_2CH_2—$ and wherein $R^2$ is an alkyl group of about 4 to 36 carbon atoms, or an aralkyl group of about 7 to 36 carbon atoms, which alkyl or aralkyl group is unsubstituted or independently substituted in available positions with oxygen, nitrogen or sulfur atoms;

$R^3$ is hydrogen or an alkyl group of about 1 to 10 carbon atoms, which alkyl group is unsubstituted or independently substituted in available positions by oxygen, nitrogen or sulfur atoms; and L is $SO_3^-$.

25. The coating composition of claim 1 wherein the surfactant is an amphoteric alkyl carboxylate, and wherein the alkyl group comprises from 8 to 22 carbon atoms.

26. The coating composition of claim 2 wherein:

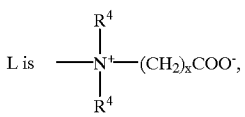

an alkyl or alkylene carboxyl group of about 1 to 8 carbon atoms which is unsubstituted or substituted in available positions by nitrogen, oxygen or sulfur atoms, and x is 1 to 4; and wherein R is a branched or straight chain alkyl group of about 4 to 36 carbon atoms or an aralkyl group of about 7 to 36 carbon atoms which alkyl or aralkyl group is unsubstituted or independently substituted in available positions with oxygen, nitrogen or sulfur atoms.

27. The coating composition of claim 1 wherein the surfactant is an alkyl phosphate mono or di-ester comprising 4 to 36 carbon atoms in each alkyl chain.

28. The coating composition of claim 2 wherein:

R is $R^2O(CH_2CH_2O)_vCH_2CH_2—$, and wherein $R^2$ is a branched or straight chain alkyl group of about 4 to 36 carbon atoms or an aralkyl group of about 7 to 36 carbon atoms, which alkyl or aralkyl group is unsubstituted or independently substituted in available positions with oxygen, nitrogen or sulfur atoms;

v is 0–100; and

L is $PO_4^{-2}$ or $PO_4^-$.

29. The coating composition of claim 1 wherein the inorganic metal oxide is selected from the group consisting of aluminum oxide, tin oxide, titanium oxide, antimony oxide, silica, zirconium oxide and mixtures thereof.

30. A coating composition according to claim 1 wherein the inorganic metal oxide comprises silica.

31. A coating composition according to claim 1 wherein the inorganic metal oxide is provided as a colloidal solution of inorganic metal oxide particles having an average particle diameter of less than 70 nm.

32. The coating composition of claim 1 further comprising a silane coupling agent capable of covalently bonding the metal oxide to the surfactant.

33. The coating composition of claim 32 wherein the silane coupling agent has the general formula:

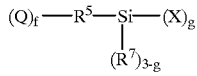

wherein:

$R^5$ is a divalent hydrocarbon bridging group of about 1 to 20 carbon atoms, optionally including in the backbone 1 to 5 moieties selected from the group consisting of —O—, —C(O)—, —S—, —SO$_2$— and —NR$^6$— groups, and optionally substituted on the backbone by —OH, —SH, and —NR$^6_2$, wherein $R^6$ is hydrogen, acetyl, or a hydrocarbon group of 1 to 6 carbon atoms;

X is —OR$^8$ where $R^8$ is an alkyl, aryl, heteroaryl or aralkyl group of 1 to 8 carbon atoms, or —N=C(R$^9$)$_2$, wherein $R^9$ is independently an alkyl, aryl or aralkyl group of 1 to 8 carbon atoms;

$R^7$ is independently an alkyl, aryl, aralkyl or alkoxy group of 1 to 8 carbon atoms which is unsubstituted or independently substituted in available positions by oxygen, nitrogen and/or sulfur atoms;

f is 0, 1, or 2;

g is 2 or 3; and

Q is a reactive functional group having one moiety selected from the group consisting of amino; hydroxyl; mercaptan; oxirane; chloro-, iodo-, and bromo-alkyl; aziridine; cyclic carboxylic anhydride; acrylate; methacrylate; acrylamide, azide, and isocyanato groups.

34. A coating composition according to claim 32 wherein the silane coupling agent has the formula

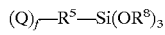

$(Q)_f$—$R^5$—$Si(OR^8)_3$ wherein:

$(Q)_f$ is a primary or secondary epoxy or amino group.

35. A coating composition according to claim 32 wherein the silane coupling agent comprises about 0.1 to 20 percent by weight of the inorganic metal oxide.

36. A coating composition according to claim 1 further comprising a wetting agent in addition to the surfactant.

37. An article comprising a substrate having a surface and a layer of a coating composition according to claim 1 on at least one surface of the substrate which coating composition has been dried.

38. An article according to claim 37 wherein the surface is plastic or glass.

39. An article according to claim 37 wherein the substrate is transparent or translucent to visible light incident thereon.

40. An article according to claim 37 wherein the substrate is selected from the group consisting of polyester, polycarbonate, allyldiglycolcarbonate, polyacrylates, polystyrene, polysulfone, polyethersulfone, cellulose acetate butyrate, glass, blends and laminates thereof.

41. An article according to claim 37 wherein the layer of the coating composition has a thickness in the range of about 500 to 2500 Å.

42. An article according to claim 37 wherein the layer of the coating composition provides a continuous network of inorganic metal oxide particles.

43. An article comprising a substrate which is transparent or translucent to visible light coated with (a) a porous inorganic metal oxide network of uniform average thickness which provides anti-reflection properties to a substrate; and (b) a surfactant having a solubility in water of less than about 10 percent by weight at 23° C. and comprised of at least one hydrophobic group and at least one hydrophilic anionic group, wherein:

(i) the hydrophilic anionic group comprises an anion selected from the group consisting of —OSO$_2$O$^-$, —SO$_2$O$^-$, —CO$_2$, (—O)$_2$P(O)O$^-$, —OP(O)(O$^-$)$_2$, —P(O)(O$^-$)$_2$, —P(O$^-$)$_2$, —OP(O$^-$)$_2$, (—SO$_2$)$_2$N$^-$, —SO$_2$N(R)$^-$, (—SO$_2$)$_2$C$^-$H, and —N$^+$(R)$_2$(CH$_2$)$_x$L', wherein R is hydrogen, an all group which is unsubstituted or substituted with atoms independently selected from the group consisting of oxygen nitrogen and sulfur, or an alkylene carboxyl group, which alkyl or alkylene carboxyl group comprises about 1 to 10 carbon atoms; x is 1 to 4; and L' is selected from the group consisting of —OSO$_2$O$^-$, —SO$_2$O$^-$, (—O)$_2$P(O)O$^-$, —OP(O)(O)$^-_2$, —P(O)(O$^-$)$_2$ and —CO$^-_2$, and wherein each anionic group is associated with or covalently bound to at least one cation which cation is selected from the group consisting of H$^+$, Na$^+$, K$^+$, Li$^+$, Ca$^{+2}$, Mg$^{+2}$, Sr$^{+2}$, Al$^{+3}$, and R"A$^+$, wherein R" is R or R' wherein R is hydrogen or an alkyl or cycloalkyl group of about 1 to 10 carbon atoms, and R' is covalently bonded to the surfactant molecule and is an alkyl bridging group of 1 to 10 carbon atoms, and A$^+$ is N$^+$R$_3$, a guanidinium ion optionally substituted with oxygen nitrogen or sulfur atoms, or N$^+$B wherein B comprises 3 to 7 atoms selected from the group consisting of carbon, nitrogen, sulfur and oxygen atoms which complete the nitrogen containing heterocyclic ring; and wherein any R or R' group may be unsubstituted or substituted with atoms independently selected from the group consisting of oxygen, nitrogen or sulfur; the cation selected such that the net charge of the surfactant molecule is neutral; and (ii) wherein the hydrophobic group comprises a hydrocarbon chain comprising at least 4 carbon atoms, or a perfluorinated radical comprising at least 3 carbon atoms; which coated substrate when coated on at least one surface with the inorganic metal oxide network in contact with the surfactant exhibits:

(1) a drop diameter of at least 4 mm when tested in accordance with the Wetting Test described herein; and (2) a percent transmission at 550 nm which is at least 3 percent greater than that of the uncoated substrate.

44. An eye shield comprising a substrate which is transparent or translucent to visible light coated with (a) a porous inorganic metal oxide network of uniform average thickness which provides anti-reflection properties to a substrate; and (b) a surfactant having a solubility in water of less than about 10 percent by weight at 23° C. and comprised of at least one hydrophobic group and at least one hydrophilic anionic group, wherein:

(i) the hydrophilic anionic group comprises an anion selected from the group consisting of —OSO$_2$O$^-$, —SO$_2$O$^-$, —CO$_2^-$, (—O)$_2$P(O)O$^-$, —OP(O)(O$^-$)$_2$, —P(O)(O$^-$)$_2$, —P(O)$_2$, —OP(O$^-$)$_2$, (—SO$_2$)$_2$N$^-$, —SO$_2$N(R)$^-$, (—SO$_2$)$_2$C$^-$H, and —N$^+$(R)$_2$(CH$_2$)$_x$L', wherein R is hydrogen, an alkyl group which is unsubstituted or substituted with atoms independently selected from the group consisting of oxygen, nitrogen and sulfur, or an alkylene carboxyl group, which alkyl or alkylene carboxyl group comprises about 1 to 10 carbon atoms; x is 1 to 4; and L' is selected from the group consisting of —OSO$_2$O$^-$, —SO$_2$O$^-$, (—O)$_2$P(O)O$^-$, —OP(O)(O)$^-_2$, —P(O)(O$^-$)$_2$ and —CO$^-_2$; and wherein each anionic group is associated with or covalently bound to at least one cation, which cation is selected from the group consisting of H$^+$, Na$^+$, K$^+$, Li$^+$, Ca$^{+2}$, Mg$^{+2}$, Sr$^{+2}$, Al$^{+3}$, and R"A$^+$, wherein R" is R or R' wherein R is hydrogen or an alkyl or cycloalkyl group of about 1 to 10 carbon atoms, and R' is covalently bonded to the surfactant molecule and is an alkyl bridging group of 1 to 10 carbon atoms, and A$^+$ is N$^+$R$_3$, a guanidinium ion optionally substituted with oxygen, nitrogen or sulfur atoms, or N$^+$B wherein B comprises 3 to 7 atoms selected from the group consisting of carbon, nitrogen, sulfur and oxygen atoms which complete the nitrogen containing heterocyclic ring; and wherein any R or R' group may be unsubstituted or substituted with atoms independently selected from the group consisting of oxygen, nitrogen or sulfur; the cation selected such that the net charge of the surfactant molecule is neutral; and (ii) wherein the hydrophobic group comprises a hydrocarbon chain comprising at least 4 carbon atoms, or a perfluorinated radical comprising at least 3 carbon atoms; which coated substrate when coated on at least one surface with the inorganic metal oxide network in contact with the surfactant exhibits:
(1) a drop diameter of at least 4 mm when tested in accordance with the Wetting Test described herein; and
(2) a percent transmission at 550 nm which is at least 3 percent greater than that of the uncoated substrate.

45. The eye shield of claim 44 wherein the inorganic metal oxide is silica and the surfactant is a perfluorinated sulfonate.

46. A surgical mask comprising a face mask and an eye shield according to claim 44.

47. A method of imparting anti-reflection and anti-fogging properties to a substrate, the method comprising the steps of:
(a) providing a substrate;
(b) preparing a coating composition comprising:
(1) an inorganic metal oxide sol capable of forming a porous network which provides anti-reflection properties to a substrate; and
(2) a surfactant having a solubility in water of less than about 10 percent by weight at 23° C. and comprised of at least one hydrophobic group and at least one hydrophilic anionic group, wherein:
(i) the hydrophilic anionic group comprises an anion selected from the group consisting of $-OSO_2O^-$, $-SO_2O^-$, $-CO_2^-$, $(-O)_2P(O)O^-$, $-OP(O)(O^-)_2$, $-P(O)(O^-)_2$, $-P(O^-)_2$, $-OP(O^-)_2$, $(-SO_2)_2N^-$, $-SO_2N(R)^-$, $(-SO_2)_2C^-H$, and $-N^+(R)_2(CH_2)_xL'$, wherein R is hydrogen, an alkyl group which is unsubstituted or substituted with atoms independently selected from the group consisting of oxygen, nitrogen and sulfur, or an alkylene carboxyl group, which alkyl or alkylene carboxyl group comprises about 1 to 10 carbon atoms; x is 1 to 4; and L' is selected from the group consisting of $-OSO_2O^-$, $-SO_2O^-$, $(-O)_2P(O)O^-$, $-OP(O)(O^-)_2$, $-P(O)(O^-)_2$ and $-CO^-_2$; and wherein each anionic group is associated with or covalently bound to at least one cation, which cation is selected from the group consisting of $H^+$, $Na^+$, $K^+$, $Li^+$, $Ca^{+2}$, $Mg^{+2}$, $Sr^{+2}$, $Al^{+3}$, and $R''A^+$, wherein R" is R or R' wherein R is hydrogen or an alkyl or cycloalkyl group of about 1 to 10 carbon atoms, and R' is covalently bonded to the surfactant molecule and is an alkyl bridging group of 1 to 10 carbon atoms, and $A^+$ is $N^+R_3$, a guanidinium ion optionally substituted with oxygen, nitrogen or sulfur atoms, or $N^+B$ wherein B comprises 3 to 7 atoms selected from the group consisting of carbon, nitrogen, sulfur and oxygen atoms which complete the nitrogen containing heterocyclic ring; and wherein any R or R' group may be unsubstituted or substituted with atoms independently selected from the group consisting of oxygen, nitrogen or sulfur; the cation selected such that the net charge of the surfactant molecule is neutral; and
(ii) wherein the hydrophobic group comprises a hydrocarbon chain comprising at least 4 carbon atoms, or a perfluorinated radical comprising at least 3 carbon atoms; wherein the metal oxide and surfactant are present in the coating composition in amounts sufficient to provide the coated light transmissive substrate
(1) with a drop diameter of at least about 4 mm when tested in accordance with the Wetting Test described herein; and
(2) with a percent transmission at 550 nm which is at least 3 percent greater than that of the uncoated substrate;
(c) applying the coating composition to at least one side of a substrate; and
(d) drying the coating composition to produce a coated substrate having a porous inorganic metal oxide network of uniform average thickness.

48. The method of claim 47 wherein the coating composition is applied to the substrate at a thickness of about 500 to 2500 Å.

49. The method of claim 47 wherein the substrate is transmissive to visible light.

50. The method of claim 47 wherein the inorganic metal oxide is silica and the surfactant is a perfluorinated sulfonate.

51. The article of claim 43 wherein the porous inorganic metal oxide network provides a continuous coating on the substrate.

52. The eye shield of claim 44 wherein the porous inorganic metal oxide network provides a continuous coating on the substrate.

53. The article of claim 43 wherein one surface of the substrate is coated with the porous inorganic metal oxide network and the surfactant and an opposite surface is coated with the porous inorganic metal oxide network, the surfactant, or a combination thereof.

54. The eye shield of claim 44 wherein one suace of the substrate is coated with the porous inorganic metal oxide network and the surfactant and an opposite surface is coated with the porous inorganic metal oxide network, the surfactant, or a combination thereof.

55. The coating composition of claim 1 wherein the melting point of the surfactant is greater than 40° C.

56. The method of claim 47 wherein the substrate surface is oxidized prior to applying the coating composition to the substrate.

57. The method of claim 47 wherein the substrate is coated with a primer prior to the application of the coating composition.

58. The article of claim 43 wherein the surfactant has a solubility in water of less than about 1 percent by weight at 23° C.

59. An article comprising a substrate which is transparent or translucent to visible light coated with
(a) a porous inorganic metal oxide network of uniform average thickness which provides anti-reflection properties to a substrate; and
(b) a surfactant having a solubility in water of less than about 10 percent by weight at 23° C. and comprised of at least one hydrophobic group and at least one hydrophilic anionic group, wherein:
(i) the hydrophilic anionic group comprises an anion selected from the group consisting of $-OSO_2O^-$, $-SO_2O^-$, $-CO_2^-$, $(-O)_2P(O)O^-$, $-OP(O)(O^-)_2$, $-P(O)(O^-)_2$, $-P(O^-)_2$, $-OP(O^-)_2$, $(-SO_2)_2N^-$, $-SO_2N(R)^-$, $(-SO_2)_2C^-H$, and $-N^+(R)_2(CH_2)_xL'$, wherein R is hydrogen, an alkyl group which is unsubstituted or substituted with atoms independently selected from the group consisting of oxygen, nitrogen and sulfur, or an alkylene carboxyl group, which alkyl or alkylene carboxyl group comprises about 1 to 10 carbon atoms; x is 1 to 4; and L' is selected from the group consisting of $-OSO_2O^-$, $-SO_2O^-$, $(-O)_2P(O)O^-$, $-OP(O)(O^-)_2$, $-P(O)(O^-)_2$ and $-CO^-_2$; and wherein each anionic group is associated with or covalently bound to at least one cation, which cation is selected from the group consisting of $H^+$, $Na^+$, $K^+$, $Li^+$, $Ca^{+2}$, $Mg^{+2}$, $Sr^{+2}$, $Al^{+3}$, and $R''A^+$, wherein $R''$ is R or R' wherein R is hydrogen or an alkyl or cycloalkyl group of about 1 to 10 carbon atoms, and R' is covalently bonded to the surfactant molecule and is an alkyl bridging group of 1 to 10 carbon atoms, and $A^+$ is $N^+R_3$, a guanidinium ion optionally substituted with oxygen, nitrogen or sulfur atoms, or $N^+B$ wherein B comprises 3 to 7 atoms selected from the group consisting of carbon, nitrogen, sulfur and oxygen atoms which complete the nitrogen containing heterocyclic ring; and wherein any R or R' group may be unsubstituted or substituted with atoms independently selected from the group consisting of oxygen, nitrogen or sulfur; the cation selected such that the net charge of the surfactant molecule is neutral; and (ii) wherein the hydrophobic group comprises a hydrocarbon chain comprising at least 4 carbon atoms, or a perfluorinated radical comprising at least 3 carbon atoms; which coated substrate when coated on at least one surface with the inorganic metal oxide network in contact with the surfactant exhibits:

(1) a drop diameter of at least 4 mm when tested in accordance with the Wetting Test described herein; and (2) a percent transmission at 550 nm which is at least 3 percent greater than that of the uncoated substrate; and wherein the article is packaged within a material which protects the article from environmental exposure.

60. The article of claim 59 wherein the packaging material is selected from the group consisting of paper, polyester, high density polyethylene and polystyrene.

61. A method of imparting anti-reflection and anti-fogging properties to a substrate, the method comprising the steps of:

(a) providing a substrate;

(b) preparing a first coating composition comprising an inorganic metal oxide sol capable of forming a porous network which provides anti-reflection properties to a substrate;

(c) preparing a second coating composition comprising a surfactant having a solubility in water of less than about 10 percent by weight at 23° C. and comprised of at least one hydrophobic group and at least one hydrophilic anionic group, wherein:

(i) the hydrophilic anionic group comprises an anion selected from the group consisting of $-OSO_2O^-$, $-SO_2O^-$, $-CO_2^-$, $(-O)_2P(O)O^-$, $-OP(O)(O^-)_2$, $-P(O)(O^-)_2$, $-P(O^-)_2$, $-OP(O^-)_2$, $(-SO_2)_2N^-$, $-SO_2N(R)^-$, $(-SO_2)_2C^-H$, and $-N^+(R)_2(CH_2)_xL'$, wherein R is hydrogen, an alkyl group which is unsubstituted or substituted with atoms independently selected from the group consisting of oxygen, nitrogen and sulfur, or an alkylene carboxyl group, which alkyl or alkylene carboxyl group comprises about 1 to 10 carbon atoms; x is 1 to 4; and L' is selected from the group consisting of $-OSO_2O^-$, $-SO_2O^-$, $(-O)_2P(O)O^-$, $-OP(O)(O^-)_2$, $-P(O)(O^-)_2$, $-CO^-_2$; and wherein each anionic group is associated with or covalently bound to at least one cation, which cation is selected from the group consisting of $H^+$, $Na^+$, $K^+$, $Li^+$, $Ca^{+2}$, $Mg^{+2}$, $Sr^{+2}$, $Al^{+3}$, and $R''A^+$, wherein $R''$ is R or R' wherein R is hydrogen or an alkyl or cycloalkyl group of about 1 to 10 carbon atoms, and R' is covalently bonded to the surfactant molecule and is an alkyl bridging group of 1 to 10 carbon atoms, and $A^+$ is $N^+R_3$, a guanidinium ion optionally substituted with oxygen, nitrogen or sulfur atoms, or $N^+B$ wherein B comprises 3 to 7 atoms selected from the group consisting of carbon, nitrogen, sulfur and oxygen atoms which complete the nitrogen containing heterocyclic ring; and wherein any R or R' group may be unsubstituted or substituted with atoms independently selected from the group consisting of oxygen, nitrogen or sulfur; the cation selected such that the net charge of the surfactant molecule is neutral; and (ii) wherein the hydrophobic group comprises a hydrocarbon chain comprising at least 4 carbon atoms, or a perfluorinated radical comprising at least 3 carbon atoms; wherein the substrate is light transmissive and the amount of metal oxide and surfactant applied to the substrate is sufficient to provide the coated substrate with (1) a porous inorganic metal oxide network of uniform average thickness;

(2) a drop diameter of at least about 4 mm when tested in accordance with the Wetting Test described herein; and (3) a percent transmission at 550 nm which is at least 3 percent greater than that of the uncoated substrate;

(d) applying either the first or second coating composition to at least one side of the substrate;

(e) allowing the coating applied in step (d) to dry;

(f) applying the coating composition not applied in step (d) to the coaling applied in step (d) on at least one side of the substrate; and (g) allowing the coating applied in step (1) to dry.

62. A method of imparting anti-reflection and anti-fogging properties to a substrate, the method comprising the steps of:

(a) providing a substrate;

(b) preparing a first coating composition comprising inorganic metal oxide particles;

(c) preparing a second coating conmposition comprising a surfactant comprised of at least one hydrophobic group and at least one hydrophilic anionic group, wherein:

(i) the hydrophilic anionic group comprises an anion selected from the group consisting of $-OSO_2O^-$, $-SO_2O^-$, $-CO_2^-$, $(-O)_2P(O)O^-$, $-OP(O)(O^-)_2$, $-P(O)(O^-)_2$, $-P(O^-)_2$, $-OP(O^-)_2$, $(-SO_2)_2N^-$, $-SO_2N(R)^-$, $(-SO_2)_2C^-H$, and $-(R)_2(CH_2)_xL'$, wherein R is hydrogen, an alkyl group which is unsubstituted or substituted with atoms independently selected from the group consisting of oxygen, nitrogen and sulfur, or an alkylene carboxyl group, which alkyl or alkylene carboxyl group comprises about 1 to 10 carbon atoms; x is 1 to 4; and L' is selected from the group consisting of $-OSO_2O^-$, $-SO_2O^-$, $(-O)_2P(O)O^-$, $-OP(O)(O^-)_2$, $-P(O)(O^-)_2$ and $-CO^-_2$; and wherein each anionic group is associated with or covaicntly bound to at least one cation, which cation is selected from the group consisting of $H^+$, $Na^+$, $K^+$, $Li^+$, $Ca^{+2}$, $Mg^{+2}$, $Sr^{+2}$, $Al^{+3}$, and $R''A^+$, wherein $R''$ is R or R' wherein R is hydrogen or an alkkyl or cycloalkyl group of about 1 to 10 carbon atoms, and R' is covalently bonded to the surfactant molecule and is an alkyl bridging group of 1 to 10 carbon atoms, and $A^+$ is $N^{+B}_3$, a guanidinium ion optionally substituted with oxygen, nitrogen or sulfur atoms, or $N^+B$ wherein B comprises 3 to 7 atoms selected from the group consisting of carbon, nitrogen, sulfur and oxygen atoms which complete the nitrogen containing heterocyclic ring; and wherein any R or R' group may be unsubstituted or substituted with atoms independently selected from the group consisting of oxygen, nitrogen or sulfur; the cation selected such that the net charge of the surfactant molecule is neutral, and (ii) wherein the hydrophobic group comprises a hydrocarbon chain comprising at least 4 carbon atoms, or a perfluorinated radical comprising at least 3 carbon atoms; wherein the substrate is light transmissive and the amount of metal oxide and surfactant applied to the substrate is sufficient to provide the coated substrate with (1) a porous inorganic metal oxide network of uniform average thickness;

(2) a drop diameter of at least about 4 mm when tested in accordance with the Wetting Test described herein; and (3) a percent transmission at 550 nm which is at least 3 percent greater than that of the uncoated substrate;

(d) applying either the first or second coating composition to at least one side of the substrate;

(e) allowing the coating applied in step (d) to dry;

(f) applying the coating composition not applied in step (d) to the coating applied in step (d) an at least one side of the substrate; and (g) allowing the coating applied in step (f) to dry.

* * * * *

UNITED STATES PATENT AND TRADEMARK OFFICE
CERTIFICATE OF CORRECTION

PATENT NO.    : 5,997,621
DATED         : December 7, 1999
INVENTOR(S)   : Matthew T. Scholz et al.

It is certified that error appears in the above-identified patent and that said Letters Patent is hereby corrected as shown below:

Column 3,
Line 44, please delete "OP(O$^-$)$_2$," and insert -- –OP(O$^-$)$_2$, -- therefor.

Column 6,
Line 37, please delete "CO$_2$" and insert -- –CO$^-$$_2$ -- therefor.
Line 37, please delete "–P(O)(O$^-$)$_2$," and insert -- –OP(O)(O$^-$)$_2$, -- therefor.

Column 13,
Line 61, please delete "he" occurring after "the surfactants of" and insert -- the -- therefor.

Column 14,
Line 45, please delete "TMN-6T" and insert -- TMN-6$^{TM}$ -- therefor.

Column 16,
Line 26-27, please delete "U.S. Pat. No. 5,595,186" and insert -- U.S. Pat. No. 5,585,186 -- therefor.

Column 21,
Table 1, column 2 entitled "Surfactant Class," Ex. No. 14, please delete "Isetnionate" and insert -- Isethionate -- therefor.

Column 22,
Table 1, column 4 entitled "Trade Name," Ex. No. 13, please delete "Zony $^{TM}$ Fse" and insert -- Zonyl $^{TM}$ FSE -- therefor.
Table 1, column 5 entitled "Source/Address," Ex. No. 24, please delete "Northflied, IL" and insert -- Northfield, IL -- therefor.

Column 23,
Table 1, column 3 entitled "Type - chemical description," Ex. No. 39, please delete "(PO$^-$ Na$^+$)" and insert -- (PO$_4^-$ Na$^+$) -- therefor.

UNITED STATES PATENT AND TRADEMARK OFFICE
CERTIFICATE OF CORRECTION

PATENT NO. : 5,997,621
DATED : December 7, 1999
INVENTOR(S) : Matthew T. Scholz et al.

It is certified that error appears in the above-identified patent and that said Letters Patent is hereby corrected as shown below:

Column 24,
Table 1, column 5 entitled "Source/Address," Ex. No. 47, 48, please delete "U.S. Pat. No. 2,109,990 (Brown)" and insert -- U.S. Pat. No. 2,809,990 (Brown) -- therefor.

Column 26,
Table 1, column 4 entitled "Trade Name," Ex. No. Comp. J, please delete "Rhodsinox™ LO" and insert -- Rhodamox™ LO -- therefor.

Column 27,
Line 22, please insert -- initially but were easily fogged after aging for only -- after "Example A and B were resistant to fogging".

Column 31,
Line 48, please delete "30.9" and insert -- 30.5 -- therefor.

Column 43,
Line 21, please delete "R=" and insert -- R is -- therefor.

Column 44,
Line 5, please insert -- wherein $R^4$ is hydrogen, or -- after "$(CH_2)_xCOO^-$,".

Column 45,
Line 49, please delete "$-CO_2$," and insert -- $-CO_2^-$, -- therefor.
Line 52, please delete "an all group" and insert -- an alkyl group -- therefor.
Line 54, please delete "oxygen nitro-" and insert -- oxygen, nitro -- therefor.

Column 46,
Line 2, please delete "oxygen nitrogen" and insert -- oxygen, nitrogen -- therefor.
Line 36, please delete "$-P(O)_2$," and insert -- $-P(O^-)_2$, -- therefor.

Column 50,
Line 48, please delete "$-(R)_2(CH_2)_xL'$," and insert -- $-N^+(R)_2(CH_2)_xL'$, -- therefor.
Line 62, please delete "alkkyl" and insert -- alkyl -- therefor.
Line 65, please delete "$N^{+B}{}_3$," and insert -- $N^+R_3$, -- therefor.

Column 51,
Line 8, please delete "neutral," and insert -- neutral; -- therefor.

UNITED STATES PATENT AND TRADEMARK OFFICE
CERTIFICATE OF CORRECTION

PATENT NO.    : 5,997,621
DATED         : December 7, 1999
INVENTOR(S)   : Matthew T. Scholz et al.

It is certified that error appears in the above-identified patent and that said Letters Patent is hereby corrected as shown below:

<u>Column 52,</u>
Line 11, please delete "in step (d) an at least" and insert -- in step (d) on at least -- therefor.

Signed and Sealed this

Twenty-third Day of March, 2004

JON W. DUDAS
*Acting Director of the United States Patent and Trademark Office*